US009987067B2

(12) United States Patent
Giordano et al.

(10) Patent No.: US 9,987,067 B2
(45) Date of Patent: Jun. 5, 2018

(54) BONE FIXATION TOOL

(71) Applicant: Zimmer, Inc., Warsaw, IN (US)

(72) Inventors: Michael Giordano, South Bend, IN (US); Antony J. Lozier, Warsaw, IN (US); Daniel P. Murphy, Claypool, IN (US)

(73) Assignee: Zimmer, Inc., Warsaw, IN (US)

( * ) Notice: Subject to any disclaimer, the term of this patent is extended or adjusted under 35 U.S.C. 154(b) by 682 days.

(21) Appl. No.: 14/413,761

(22) PCT Filed: Jul. 11, 2013

(86) PCT No.: PCT/US2013/050024
§ 371 (c)(1),
(2) Date: Jan. 9, 2015

(87) PCT Pub. No.: WO2014/011841
PCT Pub. Date: Jan. 16, 2014

(65) Prior Publication Data
US 2015/0150617 A1 Jun. 4, 2015

Related U.S. Application Data

(60) Provisional application No. 61/670,183, filed on Jul. 11, 2012, provisional application No. 61/696,461, (Continued)

(51) Int. Cl.
*A61B 17/92* (2006.01)
*A61B 17/88* (2006.01)
(Continued)

(52) U.S. Cl.
CPC .......... *A61B 17/92* (2013.01); *A61B 17/0401* (2013.01); *A61B 17/8872* (2013.01);
(Continued)

(58) Field of Classification Search
CPC ................ A61B 17/8872; A61B 17/92; A61B 2017/922; A61B 2017/924; A61B 2017/925
(Continued)

(56) References Cited

U.S. PATENT DOCUMENTS 3,584,629 A 6/1971 Hoef et al.
3,618,842 A 11/1971 Bryan
(Continued)

FOREIGN PATENT DOCUMENTS

CN 86100996 A 9/1986
CN 2145361 Y 11/1993
(Continued)

OTHER PUBLICATIONS

"U.S. Appl. No. 14/016,377, Non Final Office Action dated Feb. 17, 2016", 10 pgs.
(Continued)

*Primary Examiner* — Eric S Gibson
(74) *Attorney, Agent, or Firm* — Schwegman Lundberg & Woessner, P.A.

(57) ABSTRACT

Various embodiments of the present disclosure include a tool for stabilizing a fractured bone. The tool comprises a barrel having a proximal end and a distal end. The distal end of the barrel includes a passageway for receiving a bone pin configured to be driven into the fractured bone to stabilize the fractured bone. The passageway is sized to accommodate axial movement of the bone pin through the passageway while limiting radial movement of the bone pin in the passageway. The tool further comprises a piston having a proximal end and a distal end and configured to translate axially relative to the barrel. The proximal end of the piston includes a head and the distal end of the piston includes a needle formation, the needle formation being sized for
(Continued)

receipt within the passageway of the barrel to drive the bone pin axially from the barrel and into the fractured bone.

19 Claims, 21 Drawing Sheets

Related U.S. Application Data filed on Sep. 4, 2012, provisional application No. 61/702,815, filed on Sep. 19, 2012.

(51) Int. Cl.
    *A61B 17/04* (2006.01)
    *A61B 17/00* (2006.01)
(52) U.S. Cl.
    CPC ............. *A61B 2017/00544* (2013.01); *A61B 2017/0403* (2013.01); *A61B 2017/044* (2013.01); *A61B 2017/0409* (2013.01); *A61B 2017/924* (2013.01)
(58) Field of Classification Search
    USPC ........................................................ 606/104
    See application file for complete search history.

(56) References Cited

U.S. PATENT DOCUMENTS

| | | |
|---|---|---|
| 3,662,939 A | 5/1972 | Bryan |
| 3,752,161 A | 8/1973 | Bent |
| 3,815,476 A | 6/1974 | Green et al. |
| 3,842,839 A | 10/1974 | Malis et al. |
| 3,905,276 A | 9/1975 | Noiles et al. |
| 4,298,074 A * | 11/1981 | Mattchen ............ A61B 17/1624 173/129 |
| 4,349,028 A | 9/1982 | Green |
| 4,540,110 A | 9/1985 | Bent et al. |
| 4,728,876 A | 3/1988 | Mongeon et al. |
| 4,890,597 A | 1/1990 | Ekstrom |
| 4,901,712 A | 2/1990 | Voegell et al. |
| 4,909,419 A | 3/1990 | Yamada et al. |
| 4,915,013 A | 4/1990 | Moraht et al. |
| 4,938,408 A | 7/1990 | Bedi et al. |
| 4,951,861 A | 8/1990 | Schulze et al. |
| 5,049,775 A | 9/1991 | Smits |
| 5,080,273 A | 1/1992 | Meyer |
| 5,086,749 A | 2/1992 | Ekstrom |
| 5,125,923 A | 6/1992 | Tanner et al. |
| 5,136,469 A | 8/1992 | Carusillo et al. |
| 5,149,603 A | 9/1992 | Fleming et al. |
| 5,160,795 A | 11/1992 | Milliman |
| 5,163,519 A * | 11/1992 | Mead ................... B25B 27/026 173/135 |
| 5,265,582 A | 11/1993 | Bhogal |
| 5,282,861 A | 2/1994 | Kaplan |
| 5,330,487 A | 7/1994 | Thornton et al. |
| 5,363,834 A | 11/1994 | Stuchlik |
| 5,366,459 A | 11/1994 | Yoon |
| 5,370,037 A | 12/1994 | Bauer et al. |
| 5,398,861 A | 3/1995 | Green |
| 5,400,536 A | 3/1995 | Milliman |
| 5,415,631 A | 5/1995 | Churinetz et al. |
| 5,431,322 A | 7/1995 | Green et al. |
| 5,485,887 A | 1/1996 | Mandanis |
| 5,497,758 A | 3/1996 | Dobbins et al. |
| 5,507,750 A | 4/1996 | Goble et al. |
| 5,515,838 A | 5/1996 | Anderson |
| 5,569,264 A * | 10/1996 | Tamminmaki ....... A61B 17/068 606/104 |
| 5,613,483 A | 3/1997 | Lukas et al. |
| 5,628,444 A | 5/1997 | White |
| 5,664,552 A | 9/1997 | Kunimoto |
| 5,669,369 A | 9/1997 | Scott |
| 5,687,897 A | 11/1997 | Fa et al. |
| 5,704,150 A | 1/1998 | Milliman |
| 5,709,334 A | 1/1998 | Sorrentino et al. |
| 5,711,472 A | 1/1998 | Bryan |
| 5,755,213 A | 5/1998 | Gardner, Jr. et al. |
| 5,755,726 A | 5/1998 | Pratt et al. |
| 5,769,781 A | 6/1998 | Chappuis |
| 5,772,096 A | 6/1998 | Osuka et al. |
| 5,775,312 A | 7/1998 | Wilkinson et al. |
| 5,779,130 A | 7/1998 | Alesi et al. |
| 5,782,821 A | 7/1998 | Couch |
| 5,785,228 A | 7/1998 | Fa et al. |
| 5,803,733 A | 9/1998 | Trott et al. |
| 5,859,359 A | 1/1999 | Reid |
| 5,862,972 A | 1/1999 | Green et al. |
| 5,865,360 A | 2/1999 | White |
| 5,878,734 A | 3/1999 | Johnson et al. |
| 5,878,736 A | 3/1999 | Lotuaco, III |
| 5,896,933 A | 4/1999 | White |
| 5,902,306 A * | 5/1999 | Norman ............ A61B 17/1697 606/104 |
| 5,911,722 A | 6/1999 | Adler et al. |
| 5,913,303 A | 6/1999 | Kotsiopoulos |
| 5,918,791 A | 7/1999 | Sorrentino et al. |
| 5,924,413 A | 7/1999 | Johnson et al. |
| 5,954,259 A | 9/1999 | Viola et al. |
| 5,954,689 A | 9/1999 | Poulsen |
| 5,957,119 A | 9/1999 | Perry et al. |
| 5,957,951 A | 9/1999 | Cazaux et al. |
| 5,980,528 A * | 11/1999 | Salys .................... A61B 17/92 606/100 |
| 5,989,214 A | 11/1999 | van de Wijdeven |
| 5,997,500 A | 12/1999 | Cook et al. |
| 6,006,704 A | 12/1999 | Phillips et al. |
| 6,010,508 A | 1/2000 | Bradley |
| 6,015,078 A | 1/2000 | Almeras et al. |
| 6,016,945 A | 1/2000 | Phillips et al. |
| 6,039,231 A | 3/2000 | White |
| 6,042,571 A | 3/2000 | Hjertman et al. |
| 6,059,749 A | 5/2000 | Marx |
| 6,197,041 B1 | 3/2001 | Shichman et al. |
| 6,223,658 B1 | 5/2001 | Rosa et al. |
| 6,286,497 B1 | 9/2001 | Levkov |
| 6,306,125 B1 | 10/2001 | Parker et al. |
| 6,371,099 B1 | 4/2002 | Lee |
| 6,371,348 B1 | 4/2002 | Canlas et al. |
| 6,387,113 B1 | 5/2002 | Hawkins et al. |
| 6,470,872 B1 | 10/2002 | Tiberius et al. |
| 6,493,217 B1 | 12/2002 | Jenkins, Jr. |
| 6,532,947 B1 | 3/2003 | Rosa et al. |
| 6,578,565 B2 | 6/2003 | Casas Salva |
| 6,613,011 B2 | 9/2003 | Castellano |
| 6,620,135 B1 | 9/2003 | Weston et al. |
| 6,766,795 B1 | 7/2004 | Sullivan |
| 6,786,379 B2 | 9/2004 | Largo |
| 6,851,447 B1 | 2/2005 | Carroll |
| 6,877,647 B2 | 4/2005 | Green et al. |
| 7,066,940 B2 | 6/2006 | Riedel et al. |
| 7,069,922 B1 | 7/2006 | Orr |
| 7,172,615 B2 | 2/2007 | Morriss et al. |
| 7,237,545 B2 * | 7/2007 | Masse .................... F41B 11/57 124/73 |
| 7,320,687 B2 | 1/2008 | Lee |
| 7,427,283 B2 | 9/2008 | Roger |
| 7,441,684 B2 | 10/2008 | Shelton, IV et al. |
| 7,445,619 B2 | 11/2008 | Auge, II et al. |
| 7,448,525 B2 | 11/2008 | Shelton, IV et al. |
| 7,455,655 B2 | 11/2008 | Alexandre et al. |
| 7,481,347 B2 | 1/2009 | Roy |
| 7,665,396 B1 | 2/2010 | Tippmann, Jr. |
| 7,765,999 B1 | 8/2010 | Stephens et al. |
| 8,052,691 B2 | 11/2011 | Zwirnmann et al. |
| 8,221,433 B2 * | 7/2012 | Lozier .................. A61B 17/068 606/104 |
| 8,603,102 B2 * | 12/2013 | Lozier .................. A61B 17/068 606/104 |
| 8,852,202 B2 * | 10/2014 | Lozier .................. A61B 17/068 606/104 |
| 2001/0044637 A1 | 11/2001 | Jacobs |
| 2002/0077661 A1 | 6/2002 | Saadat |

(56) References Cited

U.S. PATENT DOCUMENTS

| | | |
|---|---|---|
| 2002/0165549 A1 | 11/2002 | Owusu-Akyaw et al. |
| 2002/0178901 A1 | 12/2002 | Bergstrom |
| 2002/0188170 A1 | 12/2002 | Santamore et al. |
| 2003/0074021 A1 | 4/2003 | Morriss et al. |
| 2003/0195498 A1 | 10/2003 | Treat et al. |
| 2003/0225411 A1 | 12/2003 | Miller |
| 2004/0138683 A1 | 7/2004 | Shelton et al. |
| 2004/0144012 A1 | 7/2004 | Adams |
| 2004/0158196 A1 | 8/2004 | Garitano et al. |
| 2004/0189258 A1 | 9/2004 | Lehmann et al. |
| 2005/0010168 A1 | 1/2005 | Kendall |
| 2005/0096661 A1 | 5/2005 | Farrow et al. |
| 2005/0119694 A1 | 6/2005 | Jacobs et al. |
| 2005/0131414 A1 | 6/2005 | Chana |
| 2005/0159752 A1 | 7/2005 | Walker et al. |
| 2005/0165394 A1 | 7/2005 | Boyce et al. |
| 2005/0188973 A1 | 9/2005 | Monks |
| 2005/0188977 A1 | 9/2005 | Wygant |
| 2005/0283189 A1 | 12/2005 | Rosenblatt |
| 2006/0124118 A1 | 6/2006 | Dobbins |
| 2006/0217729 A1 | 9/2006 | Eskridge et al. |
| 2006/0241589 A1 | 10/2006 | Heim et al. |
| 2006/0293648 A1 | 12/2006 | Herzon |
| 2007/0017497 A1 | 1/2007 | Masse |
| 2007/0021779 A1 | 1/2007 | Garvin et al. |
| 2007/0156175 A1 | 7/2007 | Weadock et al. |
| 2007/0169765 A1 | 7/2007 | Forster et al. |
| 2007/0175465 A1 | 8/2007 | Quinn et al. |
| 2007/0233133 A1 | 10/2007 | Cohen et al. |
| 2007/0235014 A1 | 10/2007 | Tiberius et al. |
| 2007/0270784 A1 | 11/2007 | Smith et al. |
| 2008/0015630 A1 | 1/2008 | Rousso |
| 2008/0029573 A1 | 2/2008 | Shelton et al. |
| 2008/0058820 A1 | 3/2008 | Harp |
| 2008/0058867 A1 | 3/2008 | Dean |
| 2008/0103355 A1 | 5/2008 | Boyden et al. |
| 2008/0125784 A1 | 5/2008 | Rabiner et al. |
| 2008/0135598 A1 | 6/2008 | Burke et al. |
| 2008/0208251 A1 | 8/2008 | Weadock et al. |
| 2008/0221580 A1* | 9/2008 | Miller ................. A61B 10/025 606/80 |
| 2008/0228104 A1 | 9/2008 | Uber et al. |
| 2008/0251569 A1 | 10/2008 | Smith et al. |
| 2008/0255607 A1 | 10/2008 | Zemlok |
| 2008/0269754 A1 | 10/2008 | Lutz et al. |
| 2008/0272172 A1 | 11/2008 | Zemlok et al. |
| 2008/0281343 A1 | 11/2008 | Dewey et al. |
| 2008/0281353 A1* | 11/2008 | Aranyi ................. A61B 17/064 606/219 |
| 2008/0283570 A1 | 11/2008 | Boyden et al. |
| 2008/0283574 A1 | 11/2008 | Boyden et al. |
| 2008/0283577 A1 | 11/2008 | Boyden et al. |
| 2008/0294024 A1 | 11/2008 | Cosentino et al. |
| 2008/0296346 A1 | 12/2008 | Shelton, IV et al. |
| 2009/0018548 A1* | 1/2009 | Charles ................. A61F 2/1662 606/107 |
| 2009/0032003 A1 | 2/2009 | Masse |
| 2009/0032568 A1 | 2/2009 | Viola et al. |
| 2009/0050671 A1 | 2/2009 | Racenet et al. |
| 2009/0082715 A1 | 3/2009 | Charles |
| 2009/0090763 A1 | 4/2009 | Zemlok et al. |
| 2009/0108048 A1 | 4/2009 | Zemlok et al. |
| 2009/0108049 A1 | 4/2009 | Roy |
| 2009/0112243 A1 | 4/2009 | Boyden et al. |
| 2009/0118734 A1 | 5/2009 | Bhatnagar et al. |
| 2009/0118738 A1* | 5/2009 | Gerondale ............ A61F 9/0008 606/107 |
| 2009/0131937 A1 | 5/2009 | Medoff |
| 2009/0163943 A1 | 6/2009 | Cavanaugh et al. |
| 2009/0171354 A1 | 7/2009 | Deville et al. |
| 2009/0206136 A1 | 8/2009 | Moore et al. |
| 2009/0209990 A1 | 8/2009 | Yates et al. |
| 2009/0235910 A1* | 9/2009 | Maeda ................. F41B 11/724 124/52 |
| 2009/0240245 A1 | 9/2009 | Deville et al. |
| 2009/0241931 A1* | 10/2009 | Masse ................. F41B 11/62 124/76 |
| 2009/0259220 A1 | 10/2009 | Appling et al. |
| 2009/0264893 A1 | 10/2009 | Beale et al. |
| 2009/0264940 A1 | 10/2009 | Beale et al. |
| 2009/0270834 A1 | 10/2009 | Nisato et al. |
| 2009/0299359 A1 | 12/2009 | Swain |
| 2010/0012698 A1* | 1/2010 | Liang ................. B25C 1/043 227/5 |
| 2010/0024791 A1 | 2/2010 | Romney |
| 2010/0030205 A1 | 2/2010 | Herzon |
| 2010/0036391 A1* | 2/2010 | Zaleski ............ A61B 1/00154 606/108 |
| 2010/0069943 A1 | 3/2010 | Roe |
| 2010/0076455 A1 | 3/2010 | Birkenbach et al. |
| 2010/0121355 A1 | 5/2010 | Gittings et al. |
| 2010/0126486 A1 | 5/2010 | Halmone et al. |
| 2010/0154767 A1 | 6/2010 | Masse |
| 2010/0305624 A1* | 12/2010 | Lozier ................. A61B 17/068 606/86 R |
| 2012/0172885 A1* | 7/2012 | Drapeau ................ A61B 17/86 606/104 |
| 2012/0232556 A1* | 9/2012 | Mani ................. A61B 17/1604 606/79 |
| 2012/0253411 A1* | 10/2012 | Lozier ................. A61B 17/068 606/329 |
| 2012/0274253 A1 | 11/2012 | Fair et al. |
| 2013/0204264 A1* | 8/2013 | Mani ..................... A61F 2/4607 606/99 |
| 2014/0074127 A1 | 3/2014 | Giordano et al. |
| 2014/0094863 A1* | 4/2014 | Lozier ................. A61B 17/068 606/86 R |
| 2014/0318823 A1* | 10/2014 | Pedicini ............. A61B 17/1604 173/201 |
| 2015/0150617 A1* | 6/2015 | Giordano ............. A61B 17/846 606/329 |
| 2015/0201918 A1* | 7/2015 | Kumar ............... A61B 17/1622 606/104 |
| 2016/0074088 A1* | 3/2016 | Mirza ................... A61B 17/92 606/62 |
| 2016/0199199 A1* | 7/2016 | Pedicini ................ A61F 2/4603 606/100 |
| 2017/0071649 A1* | 3/2017 | Lozier ................... A61B 17/88 |

FOREIGN PATENT DOCUMENTS

| | | |
|---|---|---|
| CN | 2153482 Y | 1/1994 |
| CN | 102448389 B | 10/2014 |
| CN | 106456225 A | 2/2017 |
| EP | 0171967 A2 | 2/1986 |
| EP | 0171967 A3 | 2/1986 |
| EP | 1859749 A2 | 11/2007 |
| EP | 2452631 A1 | 5/2012 |
| JP | 2017510356 A | 4/2017 |
| WO | WO-9522934 A1 | 8/1995 |
| WO | WO-0162160 A1 | 8/2001 |
| WO | WO-2008018865 A1 | 2/2008 |
| WO | WO-2010138538 A1 | 12/2010 |
| WO | WO-2014011841 A1 | 1/2014 |
| WO | WO-2015153981 A2 | 10/2015 |
| WO | WO-2015153981 A3 | 10/2015 |

OTHER PUBLICATIONS

"European Application Serial No. 10727219.7, Examination Notification Art. 94(3) dated Apr. 2, 2015", 4 pgs.

"International Application Serial No. PCT/US2013/050024, International Preliminary Report on Patentabiility dated Jan. 22, 2015", 7 pgs.

"International Application Serial No. PCT/US2015/024263, International Search Report dated Oct. 9, 2015", 6 pgs.

"International Application Serial No. PCT/US2015/024263, Written Opinion dated Oct. 9, 2015", 6 pgs.

(56) References Cited

OTHER PUBLICATIONS

"3M Staplizer Powered Metaphyse", [Online]. Retrieved from the Internet: <URL: http://www.wemed1.com/Products/spec.asp?ItemNumber=OR-3M-T100&Code=zzor3mc100>, (Accessed Apr. 22, 2013), 1 pg.

"U.S. Appl. No. 12/787,518, Notice of Allowance dated Apr. 26, 2012", 12 pgs.

"U.S. Appl. No. 12/787,518, Response filed Jan. 30, 2012 to Restriction Requirement dated Jan. 3, 2012", 2 pgs.

"U.S. Appl. No. 12/787,518, Restriction Requirement dated Jan. 3, 2012", 6 pgs.

"U.S. Appl. No. 13/493,200, Notice of Allowance dated Aug. 3, 2013", 11 pgs.

"U.S. Appl. No. 13/493,200, Response filed Jul. 3, 2013 to Restriction Requirement dated Jun. 5, 2013", 6 pgs.

"U.S. Appl. No. 13/493,200, Restriction Requirement dated Jun. 5, 2013", 8 pgs.

"U.S. Appl. No. 14/098,877, Notice of Allowance dated Jun. 4, 2014", 9 pgs.

"U.S. Appl. No. 14/098,877, Preliminary Amendment filed Jan. 23, 2014", 7 pgs.

"U.S. Appl. No. 14/098,877, Response filed May. 19, 2014 to Restriction Requirement dated Apr. 17, 2014", 8 pgs.

"U.S. Appl. No. 14/098,877, Restriction Requirement dated Apr. 17, 2014", 8 pgs.

"Chinese Application Serial No. 201080022735.4, Office Action dated Nov. 20, 2013", (W/ English Translation), 18 pgs.

"Chinese Application Serial No. 201080022735.4, Response filed Apr. 4, 2014 to Office Action dated Nov. 20, 2013", (W/ English Translation), 14 pgs.

"European Application Serial No. 10727219.7, Office Action dated Feb. 3, 2012", 2 pgs.

"European Application Serial No. 10727219.7, Office Action dated Mar. 26, 2012", 1 pg.

"European Application Serial 10727219.7, Response filed Aug. 10, 2012 to Office Action dated Feb. 3, 2012", 12 pgs.

"International Application Serial No. PCT/US2010/036126, International Preliminary Report on Patentability dated Dec. 8, 2011", 6 pgs.

"International Application Serial No. PCT/US2010/036126, International Search Report and Written Opinion dated Sep. 13, 2010", 10 pgs.

"International Application Serial No. PCT/US2013/050024, International Search Report dated Sep. 4, 2013", 3 pgs.

"International Application Serial No. PCT/US2013/050024, Written Opinion dated Sep. 4, 2013", 5 pgs.

"Polysorb™ Meniscal Stapler XLS Device", [Online]. Retrieved from the Internet: <URL: http://www.sportssurgery.com/sportsmedicine/pageBuilder.aspx?topicID=31604>, (2008), 1 pg.

"Repairing Fractured Bones by Use of Bioabsorbable Composites", Langley Research Center, Tech Briefs, [Online]. Retrieved from the Internet: <http://www.techbriefs.com/component/content/5/5?task=view>., (Sep. 2, 2006), 2 pgs.

"The Staple (Biomet's Meniscal Stapler CO2 Gun)", [Online]. Retrieved from the Internet: <URL: http://www.biomet.com/sportsmedicine/getFile.cfm?id=1055&rt=inline>, (1999), 2 pgs.

"U.S. Appl. No. 15/126,159, Preliminary Amendment Dated Sep. 14, 2016", 8 pgs.

"European Application Serial No. 16192264.6, Partial European Search Report dated Aug. 23, 2017", 18 pgs.

"International Application Serial No. PCT/US2015/024263, International Preliminary Report on Patentability dated Oct. 13, 2016", 8 pgs.

* cited by examiner

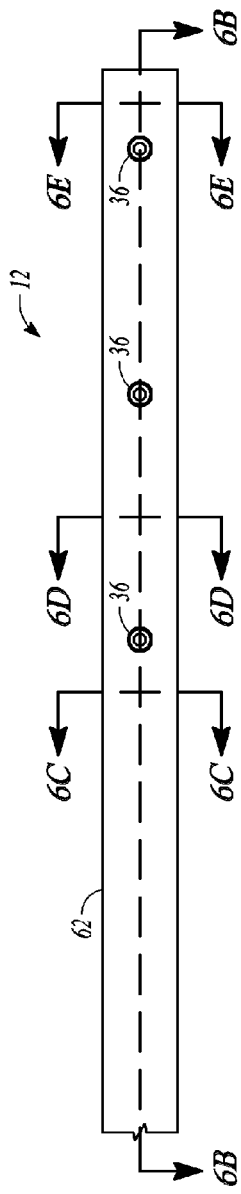
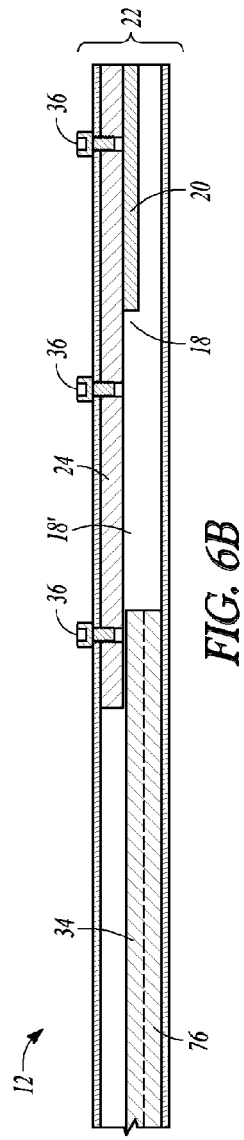
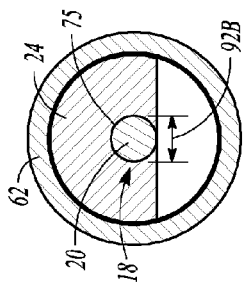
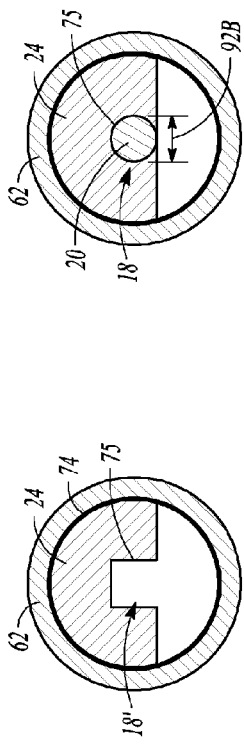
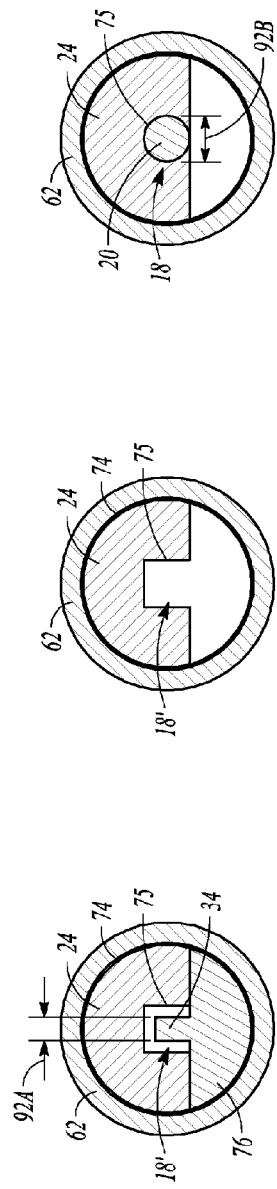

BONE FIXATION TOOL

CLAIM OF PRIORITY

This application is a U.S. National Stage Application under 35 U.S.C. 371 from International Application PCT/US2013/050024, filed on Jul. 11, 2013, and published on Jan. 16, 2014 as WO2014/011841, which claims the benefit of priority to U.S. Provisional Patent Application No. 61/670,183, filed on Jul. 11, 2012, and claims the benefit of priority to U.S. Provisional Patent Application No. 61/696,461, filed on Sep. 4, 2012, and claims benefit of priority to U.S. Provisional Patent Application No. 61/702,815, filed on Sep. 19, 2012, the benefit of priority of each of which is claimed hereby, and each of which is incorporated by reference herein in its entirety.

BACKGROUND

In trauma cases involving bone fracture, especially periarticular and comminuted (multi-part) fractures, it is important for bone fragments to be closely reassembled for proper healing to occur. Conventionally, this is accomplished using metal wires, clamps, pins, plates, screws, and retractors. As the bone fragments are put back together, temporary fixation is achieved by drilling pilot holes in the bones and passing a metal wire through the pilot holes. The wires hold the bones in place while the surgeon reassembles the fractured bone elements.

Wire installation is not a trivial task. Some wires feature a trocar tip that is used to drill through the bone; in these cases no pilot hole is needed, however it is a laborious task to slowly drill and guide the wires through bone. When the fragments have been reassembled, the surgical field is littered with wires protruding from the bones. Permanent fixation for healing is achieved with the use of bone plates and screws; the metal plates are placed on the exterior of the bones and screws are inserted to hold the pieces together.

For the temporary fixation provided by the wires to be effective, they are typically located exactly where the plates and screws need to be located. As such, there is a significant amount of pre-planning required for precise wire placement that will not interfere with the permanent means of fixation. Usually wires must be bent, removed, and repositioned so that plates can be applied effectively. Removal of the wires requires the reattachment of the installation tool which requires that the wires be unbent and straightened. The process of bending, re-bending, and un-bending the wires is not only inconvenient, it is also a waste of precious operating room time. Many aspects of using wires as temporary fixation in conventional methods adds to the total time spent in the surgery, from arduous drilling and challenging placement to difficult removal.

SUMMARY

The present inventors have recognized, among other things, that a problem to be solved can include the inconvenience and disadvantages of using wires to stabilize bone fragments in a fracture. Current devices for reducing and temporarily securing together bone fragments possess several disadvantages. External fixation devices, such as clamps, are bulky and may require invasive surgical procedures. As mentioned above, another problem can include the difficulty of driving conventional internal fixation devices, such as metallic pins and guide wires, into bone. Such devices may extend externally from the bone fragments while interfering with external plating. The present subject matter can help provide a solution to this problem, such as by providing temporary fixation to comminuted fracture fragments without hindering the installation of permanent fixation.

In other contexts, such as in gas-powered bone fixation tools, the regulation of gas pressure and airflow within the tool can be important. For example, short high-pressure bursts from a gas pressure source may be useful for driving spiral threaded bone pins into bone, while longer lower-pressure bursts may be better for screwing or for driving drill bits, for example. The present inventors have thus recognized, among other things, that a problem to be solved can include the difficulty in providing reliable gas pressure regulation in the confines of a bone fixation tool. Another problem can include the need to regulate high pressures down to a desired, usable level for successful operation of the tool in a variety of applications. The present subject matter can help provide a solution to these problems, such as by providing a small, compact gas pressure regulator capable of regulating high gas pressures in a convenient and reliable manner.

In other examples, the present inventors have recognized, among other things, that a problem to be solved can include the need to anchor bone darts securely in a bone or bone fragment when seeking to stabilize a bone fracture, for example. The present subject matter can help to provide a solution to this problem, such as by providing convenient bone dart configurations adapted to anchor a bone dart securely in a bone. Further advantages and solutions can include those discussed further below in this specification.

In this specification, the terms bone fixation element, bone pin, bone dart, and so forth are used interchangeably. Where appropriate, the terms can include other implants, surgical tools and the like.

To better illustrate the bone fixation tool disclosed herein, a non-limiting list of examples is provided here:

In Example 1, a tool for stabilizing a fractured bone comprises a barrel having a proximal end and a distal end. The distal end of the barrel includes a passageway for receiving a bone pin configured to be driven into the fractured bone to stabilize the fractured bone. The passageway is sized to accommodate axial movement of the bone pin through the passageway while limiting radial movement of the bone pin in the passageway. The tool further comprises a piston having a proximal end and a distal end and configured to translate axially relative to the barrel. The proximal end of the piston includes a head and the distal end of the piston includes a needle formation. The needle formation is sized for receipt within the passageway of the barrel and is configured to apply sufficient force to the bone pin to drive the bone pin axially from the barrel and into the fractured bone.

In Example 2, the tool of Example 1 optionally further comprises a cartridge for receiving the bone pin, the cartridge configured to be supported in the distal end of the barrel and at least partly define the passageway of the barrel.

In Example 3, the cartridge of the tool of Example 2 optionally includes an elongate semi-cylindrical body having an outer surface sized to fit within the distal end of the barrel and an inner surface at least partly defining the passageway for the bone pin.

In Example 4, the needle formation of the tool of Example 3 is optionally provided on a support member located at the distal end of the piston, the support member having a semi-circular cross-sectional shape that is complementary to the elongate semi-cylindrical body of the cartridge to fit within the distal end of the barrel.

In Example 5, the tool of any one of Examples 1 to 4 is optionally configured such that the barrel further comprises a single passageway for receiving a single bone pin configured to be driven into the fractured bone to stabilize the fractured bone.

In Example 6, the tool of any one of Examples 1 to 5 optionally further comprises a pressurized gas source for supplying a pneumatic force to the head of the piston to axially translate the piston relative to the barrel.

In Example 7, the tool of Example 6 optionally further comprises a handle configured to receive at least the pressurized gas source.

In Example 8, the tool of Example 6 optionally further comprises a handle configured to support at least the barrel or components of the barrel.

In Example 9, the tool of Example 7 or Example 8 is optionally configured such that the handle comprises a housing or housing portion axially aligned with a longitudinal axis of the barrel, the housing or housing portion including a connection port to which the pressurized gas source can be coupled.

In Example 10, the handle of the tool of any one of Examples 7 to 9 is optionally configured to be coupled to the barrel.

In Example 11, the piston of the tool of any one of Examples 1 to 10 is optionally axially translatable within the barrel.

In Example 12, the tool of any one of Examples 6 to 11 optionally further comprises a trigger assembly for releasing the piston.

In Example 13, the trigger assembly of the tool of Example 12 optionally includes a component that extends through a side wall of the barrel.

In Example 14, the component of the tool of Example 13 is optionally movable in and out of the wall of the barrel to restrain and permit, respectively, axial translation of the piston.

In Example 15, the tool of any one of Examples 12 to 14 is optionally configured such that the pressurized gas source is configured to supply pneumatic force to the head of the piston when the piston is restrained by the trigger assembly, and when driving the bone pin into the fractured bone.

In Example 16, the tool of Example 15 further comprises a reservoir for holding gas under pressure while the piston is restrained by the trigger assembly.

In Example 17, the tool of Example 16 optionally further comprises a puncture device operable to puncture, release or transfer gas from the pressurized gas source into the reservoir.

In Example 18, the barrel of the tool of any one of Examples 1 to 17 optionally includes one or more exhaust ports in a lateral side wall thereof.

In Example 19, the tool of any one of Examples 1 to 18 optionally includes a bone pin that is a polymeric bone pin, or a bone pin that includes polymeric material.

In Example 20, a kit comprises a tool according to any one of Examples 1 to 19; at least one bone pin; and a set of instructions for using one or both of the tool and the at least one bone pin.

In Example 21, the bone pin of Example 20 is optionally a polymeric bone pin, or includes polymeric material.

These and other examples and features of the present bone fixation tool will be set forth in part in the following Detailed Description.

To better illustrate the gas pressure regulator disclosed herein, a non-limiting example is provided here.

According to an example embodiment, a gas pressure regulator for regulating gas pressure within a gas-powered surgical tool is disclosed, the regulator comprising a regulator body or housing sized and configured to fit within a gas passageway within the tool; at least one inlet passageway provided in the regulator body or housing to admit pressurized gas into the regulator from an upstream pressurized gas source; a regulator mass disposed movably within the body or housing, the regulator mass having a face against which a pneumatic force generated by the pressurized gas can act to displace the mass in a first direction; a regulator spring arranged to generate a counter-force against the regulator mass in a direction opposite to the first direction; an exit port in fluid communication with a downstream side of the regulator; the regulator mass being movable under action of the pneumatic force and counter-force to open and close the exit port and regulate the gas pressure within the regulator. This example and other examples and features of the present gas pressure regulator will be set forth in part in the following Detailed Description.

This Summary is intended to provide non-limiting examples of the present subject matter. It is not intended to provide an exclusive or exhaustive explanation. The Detailed Description is included to provide further information about the present subject matter.

BRIEF DESCRIPTION OF DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various embodiments discussed in the present document.

FIGS. 6A-6E show enlarged sectional views of some components of a bone fixation tool, according to example embodiments.

DETAILED DESCRIPTION

Figure 1A:
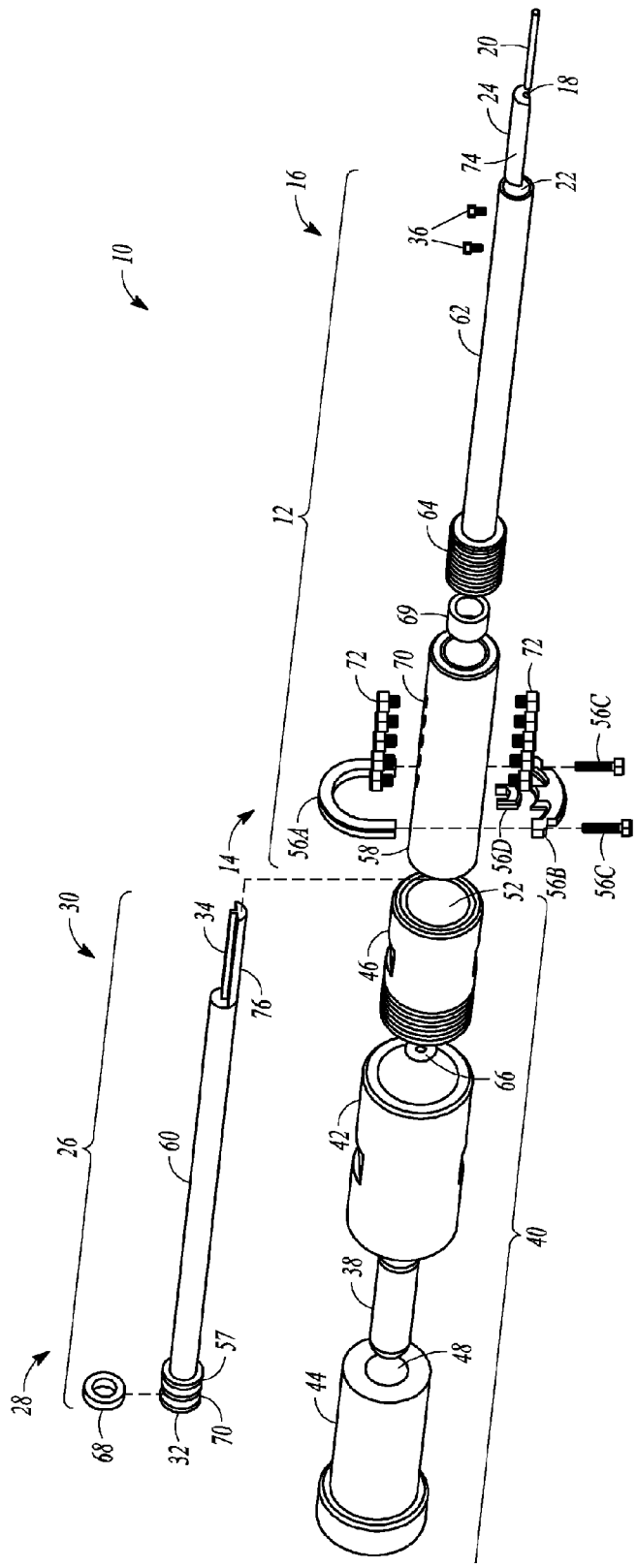
FIG. 1A shows exploded pictorial views of components of a bone fixation tool, according to example embodiments.
Figure 1B:
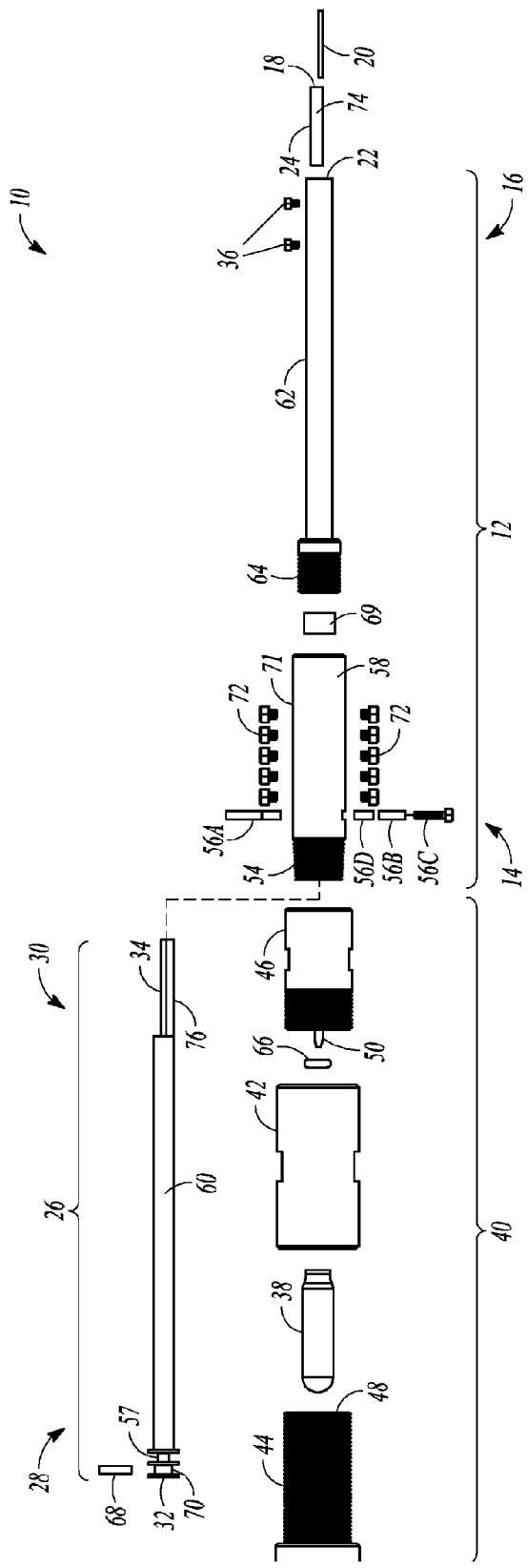
FIG. 1B shows side views of the components shown in FIG. 1A.

With reference to FIGS. 1A and 1B, an example embodiment of a bone fixation tool 10 for stabilizing a fractured bone (not shown) comprises a barrel, shown generally at 12, having a proximal end shown generally at 14, and a distal end shown generally at 16. The distal end 16 of the barrel 12 includes a passageway 18 for receiving a bone pin 20 configured to be driven into the fractured bone to stabilize the fractured bone. The passageway 18 is sized to accommodate axial movement of the bone pin 20 through the passageway while limiting radial movement of the bone pin in the passageway. In the illustrated embodiment, the barrel 12 is hollow along its entire length. A passageway for the bone pin 20 may be provided along any portion of the barrel, or be defined by any portion of the cannula of the barrel 12, or by the open mouth (or muzzle) 22 of the barrel. In some embodiments, such as the illustrated example, the passageway is defined by a component associated with the barrel, such as by a cartridge 24. The cartridge is described in later figures and description further detail below.

The tool 10 includes a piston, shown generally at 26, having a proximal end shown generally at 28, and a distal end shown generally at 30. The piston 26 is configured to fit into and translate axially within the barrel 12. The proximal end 28 of the piston 26 includes a head 32 and the distal end of the piston includes a needle formation 34. As will be discussed in more detail below, the needle formation 34 is sized for receipt within the passageway 18 of the barrel 12. In operation, the needle formation 34 is configured to apply sufficient force to the bone pin 20 to drive the bone pin axially from the barrel 12 and into the fractured bone.

The cartridge 24 receives, through its distal end, the bone pin 20. The cartridge 24 is configured to be supported in the distal end of the barrel, as shown. The cartridge at least partly defines the passageway 18 of the barrel. Other cartridge locations are possible. For example, the barrel 18 may have an extension portion (not shown) in which the cartridge can be supported. In the illustrated embodiment, the cartridge 24 is held in place at the distal end of the barrel by threaded screws 36. The cartridge 24 includes an elongate semi-cylindrical body having an outer semi-cylindrical surface 74 sized to fit within the distal end of the barrel, and an inner semi-cylindrical surface (75 in FIG. 6E) at least partly defining the passageway 18 for the bone pin, as shown.

The barrel 12 may comprise one or more additional passageways for receiving one or more additional bone pins configured to be driven into a fractured bone to stabilize the fractured bone. In the illustrated embodiment, a single passageway for receiving a single pin is provided. The relatively simple configuration of a "single shot" bone fixation tool can facilitate ease of operation and improve reliability in extreme conditions.

The tool 10 further comprises a pressurized gas source 38 for supplying a pneumatic force to the head 32 of the piston 26 to axially translate the piston relative to the barrel 12. A handle for the tool is shown generally at 40 and may comprise a number of parts as described below. The handle 40 is configured to receive the pressurized gas source 38. The gas source in this embodiment is a small, disposable gas canister of the type found in soda fountains, air guns and the like. The pressurized gas can generate a pneumatic force sufficient to drive the piston 26 and ultimately the bone pin 20 into a fractured bone.

The handle 40 of the illustrated tool comprises a cylindrical housing 42 axially aligned with a longitudinal axis of the barrel. The distal end of the housing 42 can be threaded onto a puncture device 46. A threaded cap 44 can be screwed into the proximal end of the housing 42. The threaded cap 44 has a hollow chamber 48 sized to receive the pressurized gas source 38, in this case the canister, in a tight sliding fit. A connection port (50 in FIG. 1B) for the pressurized gas source 38 is provided within the handle. The connection port 50 is carried supported by the puncture device 46 and can be connected to the pressurized gas source 38. The connection port 50 is sharp so that it can pierce a seal (not shown) of the type typically provided in the exit orifice of the gas canister 38.

The arrangement of the threaded cap 44, the housing 42, and puncture device 46 is such that insertion of the gas canister into the chamber 48 allows the cap 44 to be screwed onto the housing 42 so as to push the gas canister onto the connection port 50 and puncture the gas canister. Pressurized air is released from the canister into a holding chamber or reservoir 52 defined by the hollow volume within the puncture device 46. In the illustrated example embodiment, the reservoir 52 is defined by the cylindrical walls of the puncture device 46. Various other configurations of reservoir are possible.

In an example embodiment, a 180-degree twist of the threaded cap 44 locks the cap in place and causes the canister 38 in the chamber 48 to advance sufficiently to be punctured by the sharp connection port 50. An O-ring 66 ensures an air-tight seal between the gas canister 38 and reservoir 52. The gas canister 38 and reservoir 52 can in some embodiments together make up a pressurized gas source for a tool 10.

It will be appreciated that the volume of the reservoir 52, the initial pressure and volume of the pressurized gas source 38, and the planar area of the head 32 of the piston (on which the pressurized gas can act) can each or in combination be configured differently to adjust the force with which the bone pin 20 is driven into bone by the piston 26.

The handle 40 containing the gas source 38 is configured to be coupled to the barrel 12. In the illustrated example, this is done by screwing the handle onto the threads 54 visible in FIG. 1B. The puncture device 46 forming part of the handle 40 has internal threads (not visible) of complimentary size to engage with the threads 54 on the barrel.

The piston 26 is axially translatable within the barrel 12. The head 32 of the piston translates axially in a piston housing 58 of the barrel 12, while a stem 60 of the piston translates in a tube portion 62 of the barrel 12. The piston housing 58 and an elongate tube portion 62 of the barrel can be joined together by screw threads 64. In an example embodiment, the pressurized gas source 38 is configured to supply pneumatic force to the head 32 of the piston 26 when the piston is driving the bone pin 20 into the fractured bone. The head 32 of the piston is circular in plan outline, but other configurations are possible. An O-ring 68 carried in a slot 70 provided at or towards the proximal end 28 of the piston 26 helps to ensure an air-tight seal between the head 32 of the piston 26 and the wall of the barrel and helps to minimize escape of pressurized gas around the head 32 of the piston as the piston is driven forward. A flexible bumper 69 is provided to dampen the impact of the piston head 32 on the distal end of the piston housing 58 when driving forward. Typically, the bumper 69 is configured to provide dampening only after a bone pin 20 has been fully inserted into a bone by the piston 26, so that the pin insertion force is not prematurely reduced.

The pressurized gas in the canister 38 can apply pneumatic force directly to the head 32 of the piston 26, or (as in the embodiment shown) indirectly via the reservoir 52. It will be appreciated that in the illustrated embodiment, the head 32 of the piston 26 is of much larger surface area than the exit orifice of the canister 38 through which the gas discharges into the reservoir 52. The pressurized gas collected in the reservoir 52 thus has a relatively large effective area defined by the piston head 32 upon which to act to drive the piston 26 and ultimately the bone pin 20 with sufficient force to penetrate into bone. Greater or lesser piston forces are possible through the configuration changes described above if a more (or less) rapid or forcible entry of a bone pin 20 into bone is required. The pressurized gas source, whether constituted by the canister 38 alone or in combination with the reservoir 52 as illustrated, acts on the piston head 32 when the piston 26 is driving the bone pin 20 into a fractured bone.

In the illustrated example, the pressurized gas source is also configured to apply a pneumatic force to the head of the piston in a "ready-to-fire" state of the tool 10. In this state, the piston 26 is temporarily restrained by a trigger assembly before being fired. The components of the trigger assembly are denoted by the reference numeral 56.

In the illustrated embodiment, the trigger assembly comprises two opposed clamp pieces 56A and 56B which are secured together by threaded bolts 56C which can be screwed through holes in clamp 56B into threaded holes provided in clamp 56A. The clamped pieces 56A and 56B support a detent element or firing button 56D which can be pushed inwardly by a user to release the piston and "fire" the tool to drive the bone pin 20 into bone. The detent 56D extends through a side wall of the barrel. The detent 56D is movable in and out of the wall of the barrel to engage with the walls of a slot 57 provided at the proximal end 28 of the piston 26. Movement of the detent 56D in or out serves to restrain or permit, respectively, axial translation of the piston 26 within the barrel 12. Actuation of the trigger assembly by pushing in the detent 56D releases the piston 26 so that pressurized gas within the reservoir 52 (which in this example embodiment acts on the head 32 of the piston 26 even in the "ready-to-fire" state) is free to drive the piston 26 down the barrel 12 and drive the bone pin 20 into bone.

The piston housing 58 of the barrel includes one or more exhaust ports 71 in a lateral side wall thereof. The ports 71 can be opened or closed by one or more plugs 72 which fit into the ports 71. The exhaust ports 71 allow air downstream of the piston head 32 to escape from the barrel 12. Closing or opening one or more ports 71 can adjust the rate of escape of downstream air, and in turn, adjust the speed and driving force of the piston 26 as desired. Opening an initially downstream port 71 which is to be passed by the piston head 32 as the head travels down the barrel 12 can also vent gas on the (now) upstream side of the head 32 such that the pneumatic force driving the piston 26 is reduced or removed accordingly by virtue of the venting of pressurized gas. In this arrangement, the piston 26 can proceed to drive the bone pin 20 at least partially under the momentum of its own mass. The piston 26 accordingly acts as a movable or impact mass for the tool 10.

As mentioned above, the distal end 30 of the piston 26 includes a needle formation 34. In the illustrated embodiment, the needle formation 34 is an elongate pin-shaped structure, having a thin, rectangular outline in plan and a substantially square transverse cross-section. Other cross-sectional shapes are possible. The square cross-sectional area of the needle formation 34 is approximately the same size as (or smaller than) the circular cross-sectional area of the bone pin 20. In being sized accordingly, the needle formation 34 is able drive the bone pin 20 down at least a portion of the passageway 18 in the barrel and out of the open mouth 22 of the barrel into an adjacent bone. Various types or configuration of needle formation 34 are possible in order to act on the bone pin 20. For example, the needle formation 34 may be of circular cross-section, or be provided in a number of different lengths or materials. For example, the needle formation 34 may be changeable within the tool 10 to work with different types or lengths of bone pin 20.

In the illustrated embodiment, the needle formation 34 is provided on a support member 73 located at the distal end of the piston 26. The support member 73 has a semi-circular cross-sectional shape that is complementary to the semi-cylindrical body of the cartridge 24 to fit within the distal end of the barrel 12. Other configurations of support member are possible. In some embodiments, the needle formation 34 does not have a support member 73, while in some embodiments the support member 76 is be integral with or separately formed from the needle formation 34.

In using the tool 10 illustrated in FIGS. 1A and 1B, a user can load a gas canister 38 into the volume 48 in the threaded cap 44, and screw the loaded cap 44 onto the back of the housing 40 of the handle, as described above. As the cap 44 is screwed in place, the gas canister 38 advances within the handle 40 to be punctured by the sharp connection port 50 on the puncture device 46. This releases a charge of pressurized gas into the reservoir 52. The charge of pressurized gas acts on the head 32 of the piston 26, but the piston cannot move initially as it is held in place by the trigger assembly, and more specifically the detent 56D. The user can then load a bone pin 20 of desired length into the passageway 18 in the cartridge 34 supported in the open mouth 22 of the barrel 12. It will be appreciated that a user may prefer to load a bone pin 20 into the cartridge 34 before installing a gas canister 38 into the tool 10, or pressuring the reservoir 52. In being loaded at the distal end 16 of the barrel 12, the tool 10 is in effect a "muzzle loader". In some embodiments, a "breech-loading" or side-barrel configuration is possible.

Once loaded, the mouth 22 of the barrel 12 can be brought adjacent a bone at a desired location at an injury site. The tool is "fired" by actuating the trigger assembly 56, and the released piston 26 drives the bone pin 20 into the bone under action of pneumatic forces, as described above. A series of bone pins 20 may be driven into bone, one at a time, in this manner. In some example embodiments, the pressurized gas source 38 and reservoir 52 are configured such that a single gas canister 38 can drive several one pins in multiple operations of the tool. In some embodiments, the tool 10 may be configured to hold or fire more than one bone pin 20, in a "repeat fire" configuration.

Figure 2A:
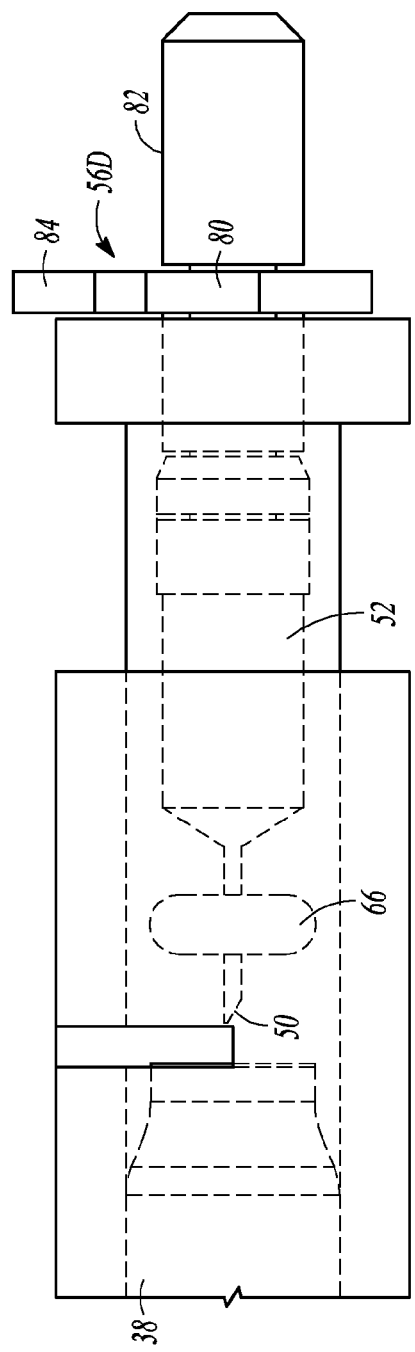
FIGS. 2A-2B show side and sectional views of some components of a bone fixation tool, according to example embodiments.
Figure 2B:
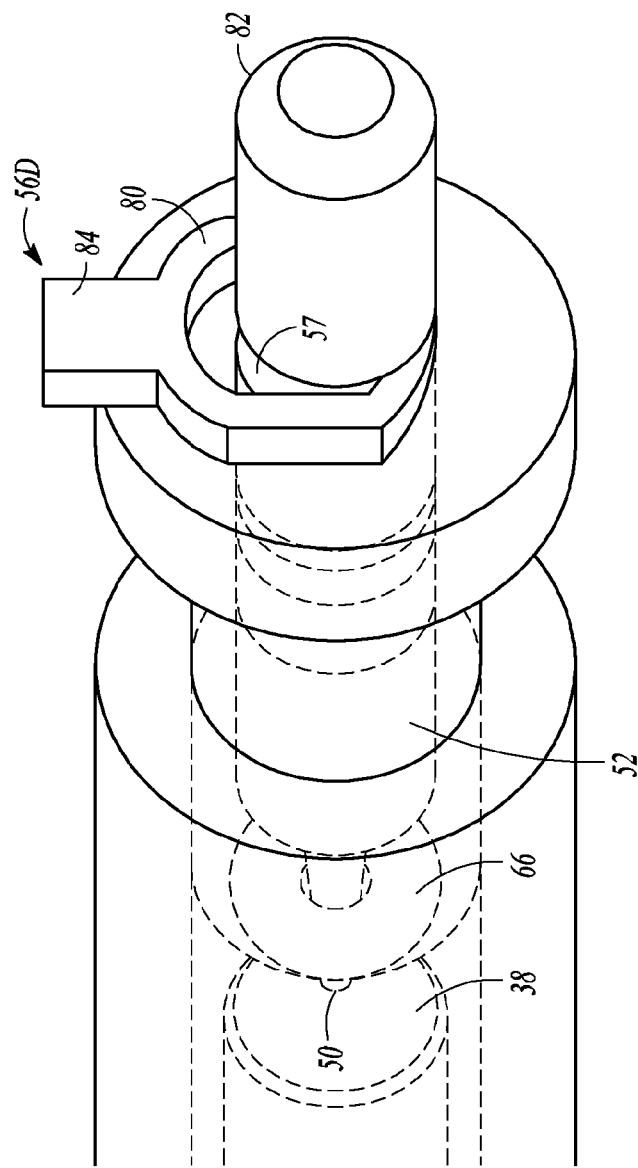

Tool 10 may be powered pneumatically, hydraulically, electrically (e.g. with batteries), and/or electromagnetically. Other sources of power are also possible, such as a compression spring, external hydraulic power source or electric motor, for example. Manual generation of force is also possible in some example embodiments. Such configurations can work like an impact hammer or wrench in which movement is manually imparted to a movable mass (such as a piston 26 or separate mass) which then impacts on a pin to drive the into the bone or other material. One such movable mass is shown at 82 in FIGS. 2A-2B.

In these views, like numerals are used to refer to like or similar parts. For example, a pressurized gas canister 38, O-ring 66, and reservoir 52 are visible. As described above, such components can form part of a pressurized gas source for applying pneumatic force to a piston 26. The views also depict an alternate form of trigger detent 56D. Here, the detent 56D has an oval ring 80 which can engage in a slot 57 to restrain axial movement of the movable mass 82 or, in other embodiments, the movement of a piston 26 of the type described and illustrated above. The ring 80 can be moved out of engagement of the slot 57 by depression of the firing button 84.

Figure 3A:
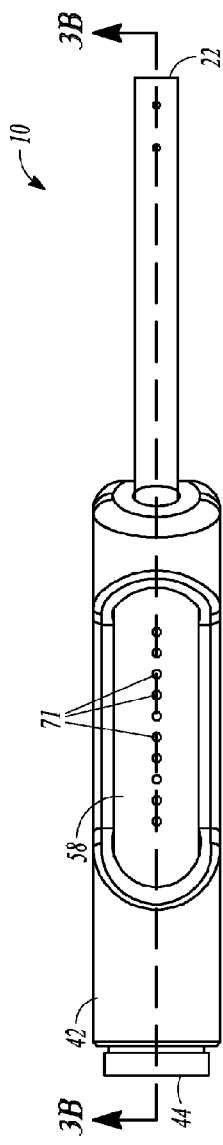
FIGS. 3A-3C show top, side sectional, and exploded sectional views respectively of a bone fixation tool, according to example embodiments.
Figure 3B:
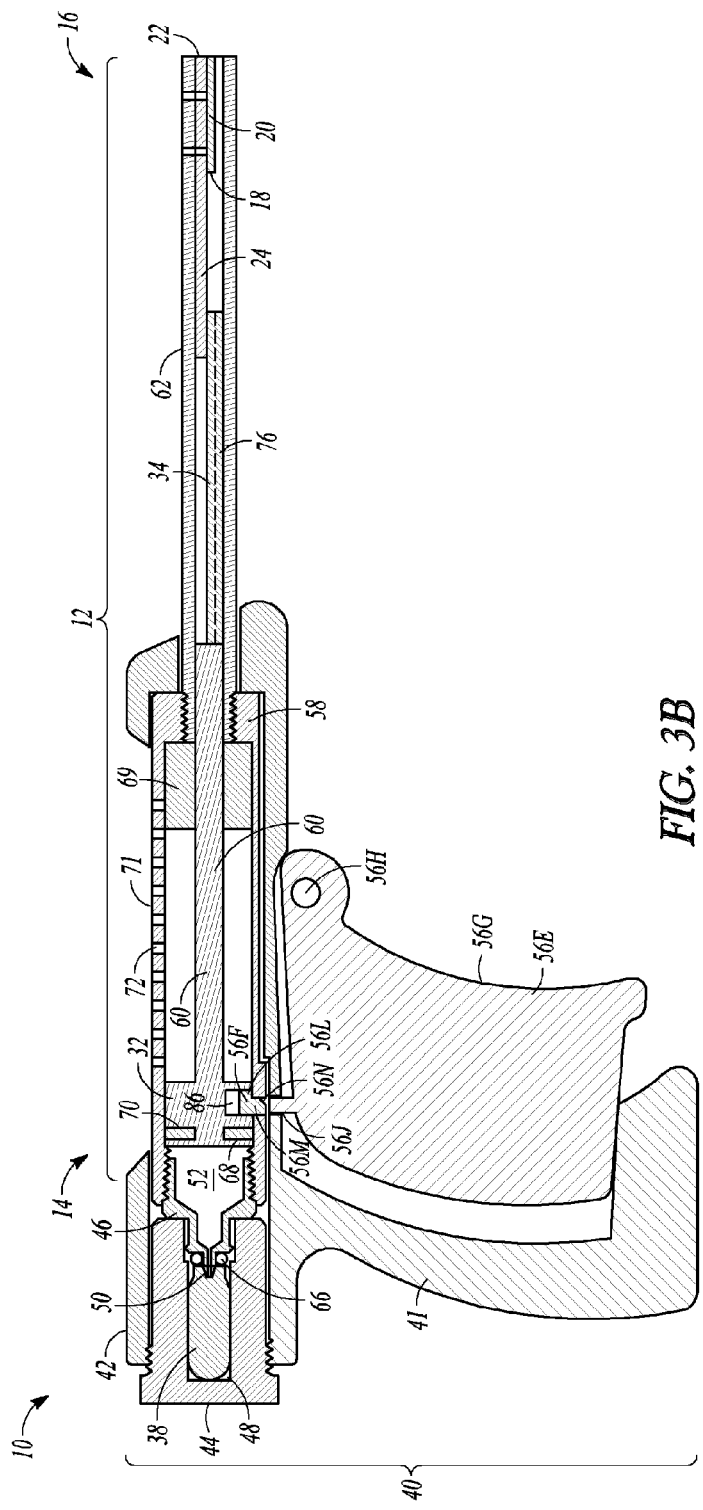
Figure 3C:
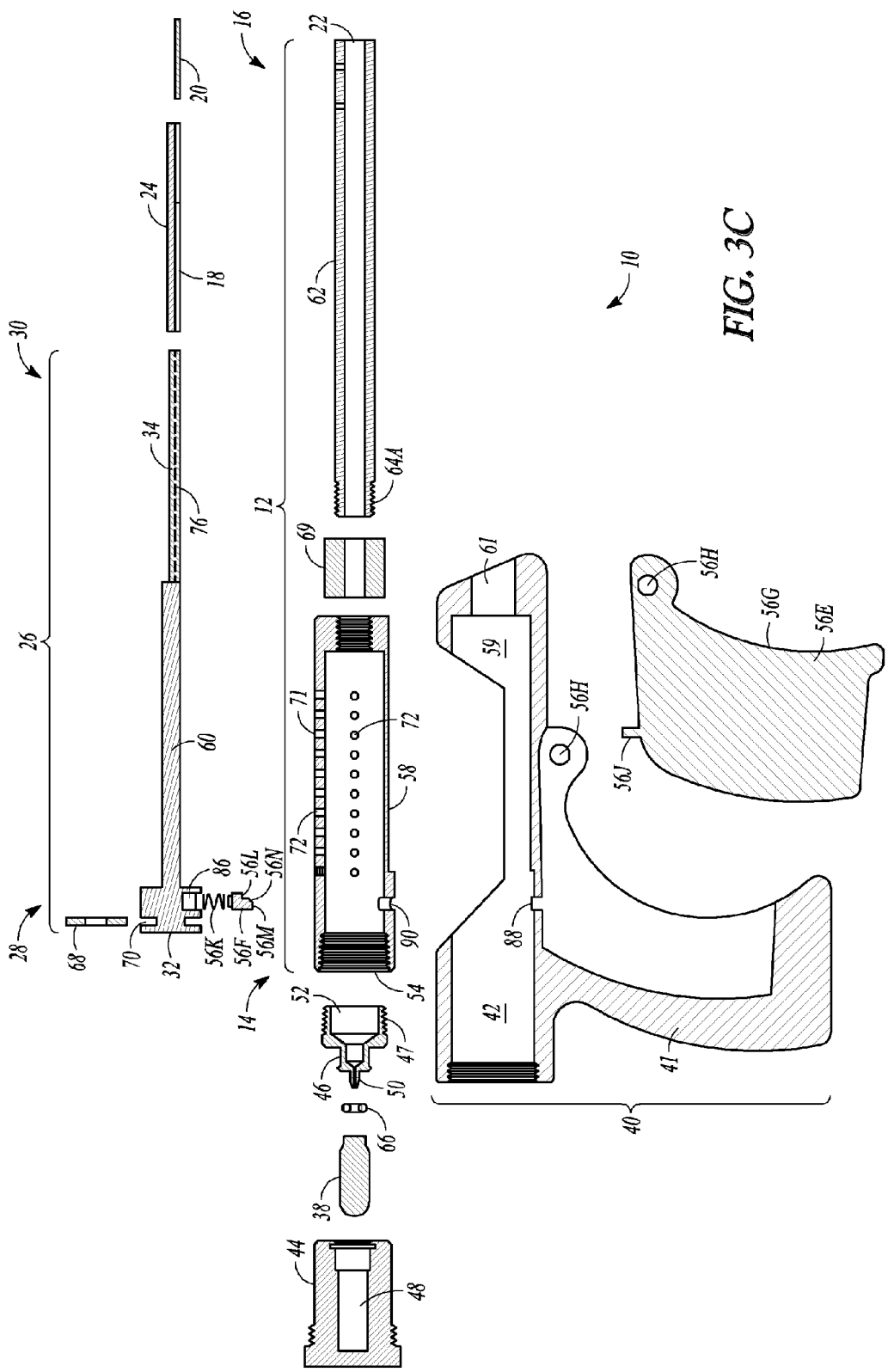

Reference is now made to FIGS. 3A-3C which show an example embodiment of a bone fixation tool 10 of the present disclosure. Like numerals are used to describe similar components. In FIG. 3A a plan view of the tool is visible. A sectional view is shown in FIG. 3B and an exploded sectional view in FIG. 3C. This embodiment of a tool has the general appearance of a hand gun.

This example embodiment of a tool 10 for stabilizing a fractured bone (not shown) comprises a barrel, shown generally at 12, having a proximal end shown generally at 14, and a distal end shown generally at 16. The distal end 16 of the barrel 12 includes a passageway 18 (visible in FIG. 3B) for receiving a bone pin 20 configured to be driven into the fractured bone to stabilize the fractured bone. The passageway 18 is sized to accommodate axial movement of the bone pin 20 through the passageway 18 while limiting radial movement of the bone pin 20 in the passageway 18.

In the illustrated embodiment, the barrel 12 is hollow along its entire length. As with the embodiment described above, a passageway 18 for the bone pin 20 may be provided by, or extend through, any portion of the cannula of the hollow barrel 12, or the open mouth or muzzle 22 of the barrel. In some embodiments, such as the illustrated example, the passageway 18 is at least partially defined by a component associated with the barrel, such as a cartridge 24. The cartridge is described in further detail below with reference to FIG. 6.

The tool 10 includes a piston 26 having a proximal end shown generally at 28, and a distal end shown generally at 30. The piston 26 is configured to translate axially relative to the barrel 12. The proximal end 28 of the piston 26 includes a head 32 and the distal end of the piston includes a needle formation 34. As will be described further below, at least a part of the needle formation 34 is sized for receipt within the passageway 18 of the barrel 12. In operation, the needle formation 34 is configured to apply sufficient force to the bone pin 20 to drive the bone pin axially from the barrel 12 and into the fractured bone.

The cartridge 24 receives the bone pin 20 and is configured to be supported in the distal end of the barrel, as shown. The cartridge at least partly defines the passageway 18 of the barrel. Other cartridge locations are possible. For example, the barrel 18 may have an extension or muzzle portion (not shown) in which the cartridge can be supported. In the illustrated embodiment, the cartridge 24 is held in place at the distal end of the barrel by grub screws (not shown). The barrel 12 may comprise one or more additional passageways for receiving one or more additional bone pins configured to be driven into a fractured bone to stabilize the fractured bone. In the illustrated embodiment, a single passageway for receiving a single pin is provided.

The tool 10 further comprises a pressurized gas source 38 for supplying a pneumatic force to the head 32 of the piston 26 to axially translate the piston relative to the barrel 12. A handle for the tool is shown generally at 40 and includes a hand grip portion 41. The handle 40 may support a number of parts as described below.

The handle 40 is configured to receive the pressurized gas source 38. The gas source in this embodiment is a convenient, disposable gas canister of the type found in soda fountains, air guns and the like. The pressurized gas within the canister can generate a pneumatic force sufficient to drive the bone pin 20 into a fractured bone.

The handle 40 of the illustrated tool includes a part-cylindrical housing portion 42 axially aligned with a longitudinal axis of the barrel. A threaded cap 44 (also termed a puncture screw) can be screwed into the proximal (or back) end of the housing portion 42. The other end of the cap 44 can be screwed onto a hollow, cylindrical puncture device 46. The threaded cap 44 has a hollow chamber 48 sized to receive the pressurized gas source, in this case the canister 38, in a sliding fit. A connection port 50 for the pressurized gas source 38 is provided within the handle. The connection port to which the pressurized gas source can be coupled is carried in the puncture device 46 within the handle. The connection port 50 is sharp so that it can puncture a seal (not shown) provided in the exit orifice of the gas canister. The puncture device 46 has threads 47 that can engage with complementary threads 54 on a piston housing 58 described in more detail below.

The arrangement of the threaded cap 44, the housing portion 42, and puncture device 46 is such that insertion of the gas canister into the chamber 48 allows the cap 44 to be screwed into the housing portion 42 so as to push the gas canister onto the sharp connection port 50 and puncture the gas canister. Pressurized gas is released from the punctured canister into a holding chamber or reservoir 52 which is at least partially defined within the puncture device 46. In the illustrated example embodiment, the reservoir is at least partly defined by the cylindrical walls of the puncture device 46, and at least partly defined by the cylindrical walls of the piston housing 58. Various other configurations of reservoir are possible. The reservoir may be a separate component of the tool.

In an example embodiment, a 180-degree twist of the threaded cap 44 locks the cap 44 in place in the housing portion 42 of the handle, and causes the canister in the chamber 48 to advance sufficiently to be punctured by the sharp connection port 50. An O-ring 66 helps to ensure an air-tight seal between the gas canister 38 and reservoir 52. The gas canister 38 and reservoir 52 can in various embodiments together make up a pressurized gas source for a tool 10. It will be appreciated that the volume of the reservoir 52, the initial pressure and volume of the pressurized gas source 38, and the planar area of the head 32 of the piston (acted on by the pressurized gas) can each or in combination be configured differently to adjust the force with which the bone pin 20 is driven into bone by the piston.

The handle 40 is also configured to support various components of the barrel 12. In the illustrated example, it will be appreciated that mounting the barrel components in the handle 40 can be accomplished by assembling the initially separate components inside the handle. The components can be removed from the handle 40 by being disassembled. Once installed inside the handle, the piston housing 58 is engaged (at its distal end) in a close fit within an appropriately shaped recess 59 provided within the handle, and (at its proximal end) at least partially within the housing portion 42 of the handle. A portion of a tube portion 62 of the barrel extends through an aperture 61 in the handle 40.

The piston 26 is axially translatable within the barrel 12. The head 32 of the piston translates axially in the piston housing 58 of the barrel 12, while a stem 60 of the piston translates in a tube portion 62 of the barrel 12. The piston housing 58 and tube portion 62 of the barrel can be joined together by screw threads 64A and 64B. In an example embodiment, the pressurized gas source is configured to supply pneumatic force to the head 32 of the piston 26 when the piston is driving the bone pin into the fractured bone 26. The head of the piston is circular in plan outline, but other configurations are possible. An O-ring 68 carried in a slot 70 provided at or towards the proximal end 28 of the piston helps to ensure an air-tight seal between the head 32 of the piston 26 and the wall of the barrel 12 and helps to minimize escape of pressurized gas around the head of the piston as the piston is driven forward. A bumper 69 is provided to dampen the impact of the piston head 32 on the distal end of the piston housing 58. Typically, dampening will only occur after a bone pin has been fully inserted into a bone by the piston.

The pressurized gas in the canister 38 can apply pneumatic force directly to the head 32 of the piston 26, or indirectly via the reservoir 52. It will be appreciated that in the illustrated embodiment, the head 32 of the piston 26 (on which the gas acts) is of much larger surface area than the exit orifice of the canister through which the gas discharges into the reservoir. The collected gas in the reservoir thus has a relatively large effective area defined by the piston head 32 upon which to act to drive the piston and the bone pin with sufficient force into bone or other material. Greater piston forces are possible by making the configuration changes described above if a more (or less) rapid or forcible entry of a bone pin into bone is required.

The pressurized gas source, whether constituted by the canister 38 alone or in combination with the reservoir 52 as illustrated, acts on the piston head 32 when the piston 26 is driving the bone pin 20 into a fractured bone. In the illustrated example, the pressurized gas source is also configured to apply a pneumatic force to the head of the piston in a "ready-to-fire" state of the tool 10.

In this state, the piston 26 is temporarily restrained by a trigger assembly before being fired. The components of the trigger assembly are denoted by the reference numeral 56. In the illustrated embodiment, the trigger assembly comprises a trigger 56E, and a spring loaded detent or button 56F. The trigger 56E has a curved, leading edge 56G that can be pulled by a user's fingers to actuate the trigger assembly, and an aperture 56H that allows the trigger to be mounted pivotally in the handle 40. The trigger 56E also has a cam formation 56J that can act (through apertures 88 and 90 in the handle 40 and piston housing 58, respectively) against the spring loaded detent 56F when the trigger is pulled.

As shown more clearly in FIG. 3B, the spring loaded detent lies in a recess 86 in the piston head 32. The detent 56F is biased out of the recess by a spring 56K (visible in FIG. 3C). A step 56L prevents the detent from falling out of the piston head, and a nose portion 56M of the detent extends through an aperture in the wall of the piston housing where it can engage with the cam 56J on the trigger. The nose portion is chamfered at 56N. As the cam 56J moves up with clockwise rotation of the pulled trigger 56E (as viewed in FIGS. 3B and 3C), the detent 56F is pushed into the recess 86 in the piston head and the nose portion 56M of the detent is withdrawn out of the aperture 90 in the piston housing 58. This withdrawal of the detent 56F releases the piston 26 to translate axially down the barrel 12 under the action of the forces generated by the pressurized gas source 38 to drive the bone pin 20 into bone.

Referring again to FIGS. 3B and 3C, the piston housing 58 of the barrel includes one or more exhaust ports 71 in a lateral side wall thereof. The ports can be opened or closed by one or more plugs (not shown in FIGS. 3A-3C) which fit into the ports. The exhaust ports allow air downstream of the piston head (i.e. nearer the open mouth 22 of the barrel) to escape from the barrel. Closing or opening one or more ports 71 can adjust the rate of escape of downstream air, and in turn, adjust the speed and force of the piston as desired. Opening an initially downstream port which is to be passed by the piston head 32 as the head travels down the barrel can also release gas on the upstream side of the head 32 such that the pneumatic force driving the piston 26 is reduced or removed accordingly. In such a situation, the piston 26 can proceed as necessary to drive the bone pin 20 at least partially under the momentum of its own mass. In this way, the piston constitutes a movable or impact mass for the tool 10.

Figure 4A:
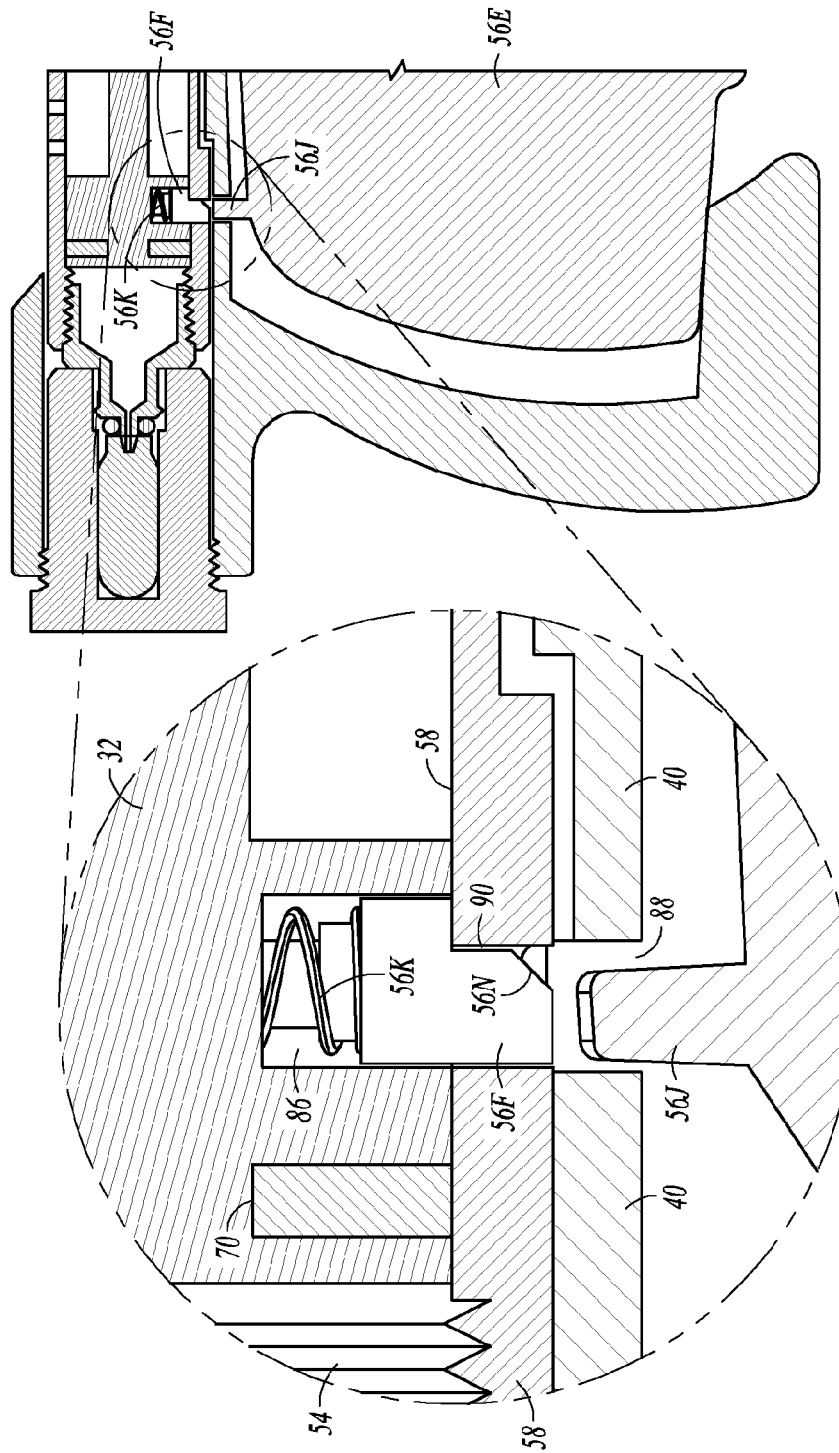
FIGS. 4A-4C show enlarged sectional views of some components of a bone fixation tool, according to example embodiments.
Figure 4B:
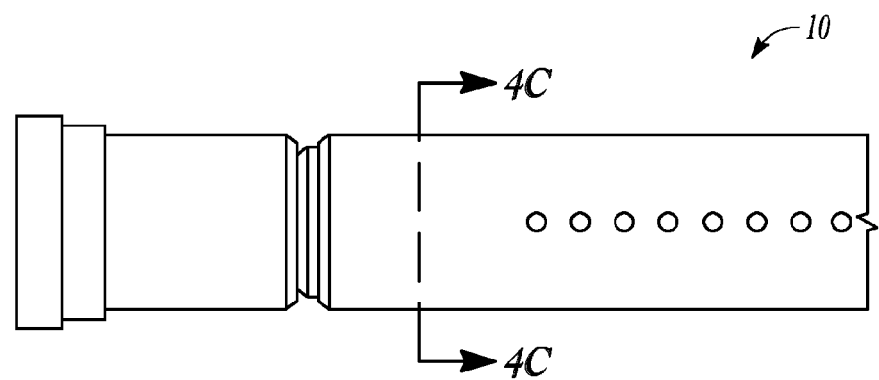
Figure 4C:
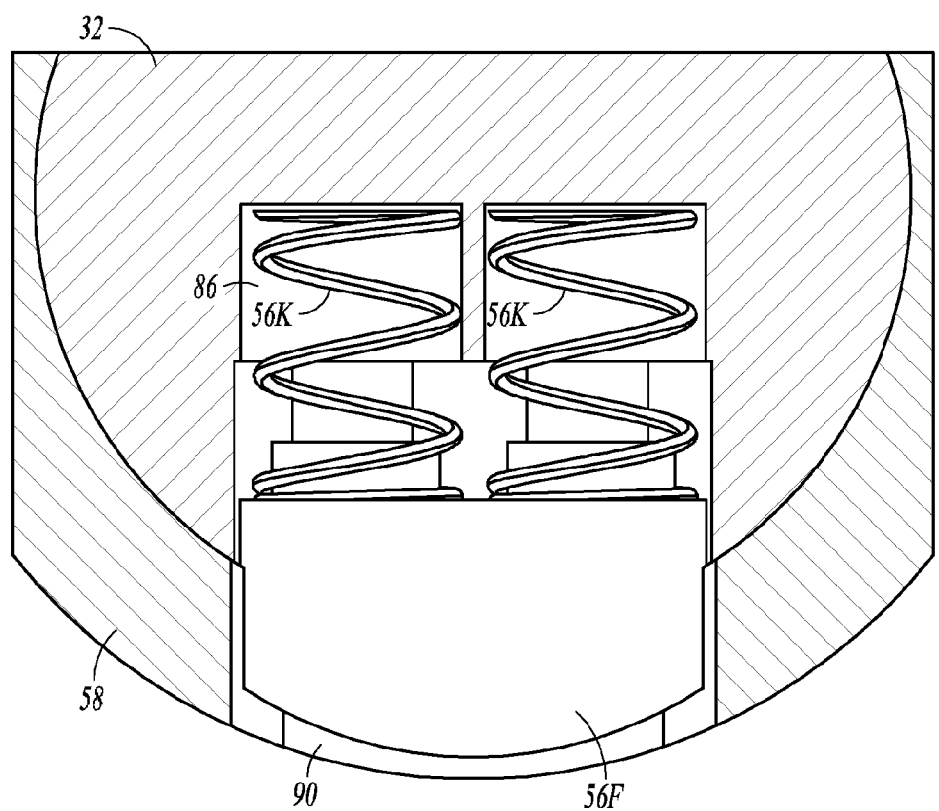

Enlarged sectional views of the trigger assembly components are shown in FIGS. 4A and 4C. FIG. 4C is a cross-sectional view taken at the line 4C-4C in FIG. 4B. In these views, like numerals refer to like (or similar) parts.

Figure 5:
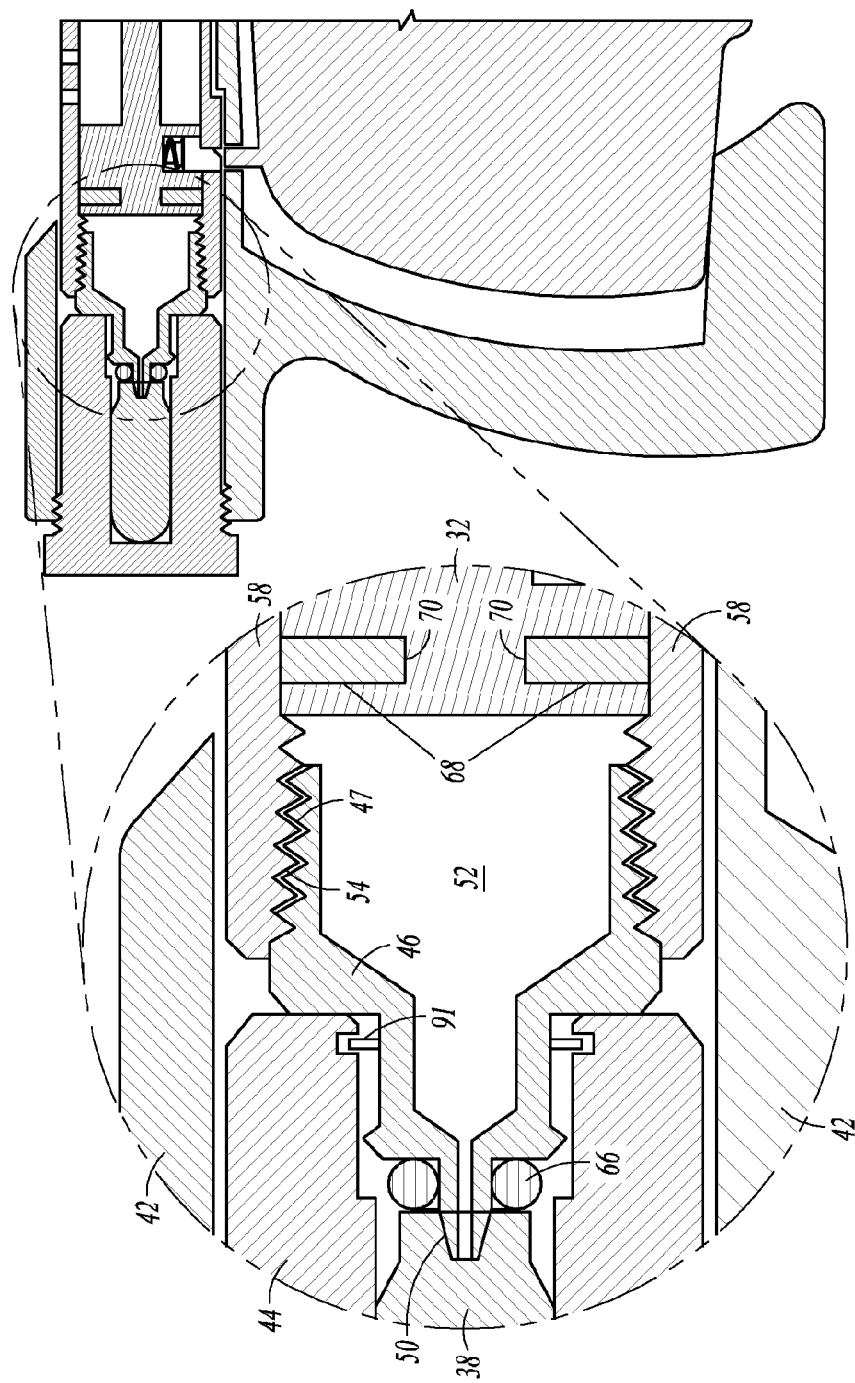
FIG. 5 shows an enlarged sectional view of some components of a bone fixation tool, according to example embodiments.

An enlarged sectional view of some components associated with the pressurized gas source 38 and driving the piston 26 are illustrated in FIG. 5. Again, like numerals refer to like or similar parts. Visible in the enlarged view of FIG. 5 are, for example, the gas canister 38, the threaded cap 44, the O-ring 66, the sharp connection port 50, the puncture device 46 and the reservoir 52. Also visible in this view is a further O-ring 91 provided in the joint between the threaded cap 44 and the puncture device 46. Also visible in the view are the piston head 32 and the O-ring 68 situated in the annular slot 70 formed in the piston head. The piston housing is shown at 58.

As mentioned above, the distal end 30 of the piston 26 includes a needle formation 34. The needle formation 34 and cartridge 24 are shown more clearly in FIGS. 6A-6E of the accompanying drawings. Again, like numerals refer to like or similar parts.

In the illustrated embodiment, the needle formation 34 is an elongate pin-shaped structure, having a thin, rectangular outline in plan and a substantially transverse square cross-section (visible more clearly in FIG. 1A). Other shapes of needle formation are possible. For example, the needle formation 34 might resemble a pin or nail having a circular cross-section for example. The substantially square cross-section of the illustrated embodiment of the needle formation 34 can be seen more clearly in the enlarged view given in FIG. 6C. The needle formation 34 travels in and guided by a portion of the passageway 18 (marked 18' in the figures) which also has a substantially square outline, at least at the sectional locations shown. The transverse width 92A of the needle formation 34 is approximately the same size as, or smaller than, the transverse width 92B (see FIG. 6C) of a open slot or groove formed in the bottom of the portion of the passageway 18 (of circular cross-section) that guides the bone pin 20 at the distal end of the barrel 12. Dimension 92A can be seen in FIG. 6C and dimension 92B can be seen in FIG. 6E. In being sized accordingly, the needle formation 34 can travel down both the passageways 18' and 18 in the barrel and drive the bone pin 20 out of the open mouth 22 of the barrel 12 into an adjacent bone. In some embodiments, the distal end of the needle formation 34 is able to travel fully up to (and in some cases, even outside) the open mouth 22 of the barrel 12.

In the illustrated embodiment in FIG. 6, the cartridge 24 includes an elongate semi-cylindrical body having an outer semi-cylindrical surface 74 sized to fit within the distal end of the barrel, and one or more inner surfaces 75 at least partially defining the passageways 18 and 18' for the bone pin, as shown. In an example embodiment, the needle formation 34 is provided on a support member 76 located at the distal end of the piston. As shown, the support member 76 has a semi-circular cross-sectional shape that is complementary to the semi-cylindrical body of the cartridge 24 to fit together within the distal end of the barrel 12.

As with the embodiment shown in FIGS. 1A and 1B, various types or configuration of needle formation 34 are possible. For example, the needle formation may be of circular cross-section, or be provided in a number of different lengths or materials. The needle formation 34 may be changeable within the tool 10 to work with different types or lengths of bone pin 20. It will be appreciated that the needle formation 34 could, for example, be centrally placed within the passageway without a support configuration, or could be configured to pass through other regions within the passageway 18 and 18' and be supported or configured accordingly. A supported needle formation design can be used to assist the needle formation in resisting buckling under the impact loads imposed during bone pin delivery.

In using the tool 10 illustrated in FIG. 3A-6E, a user loads a gas canister 38 into the threaded cap 44, and screws the cap into the back of the housing 40 of the handle. As the cap 44 is screwed in, the gas canister is punctured by the connection port 50 on the puncture device 46 to release a charge of pressurized gas into the reservoir 52. The charge of pressurized gas acts on the 32 of the piston, but the piston cannot move as it is temporarily held in place by the trigger assembly, and specifically the detent 56F. The user then loads a bone pin (of desired length) into the open mouth 22 of the barrel 12. It will be appreciated that a user may prefer to load a pin into the open mouth of the barrel before loading the gas canister, or pressuring the reservoir. Either method is possible.

The mouth of the barrel is brought adjacent a bone at a desired location at an injury site. The tool is "fired" by actuating the trigger assembly, and the released piston drives the loaded bone pin into the bone under action of the pneumatic force, as described above. A series of pins may be driven into bone, or other structure, in this manner. In addition to securing together bone fragments, the methods described above may also be used to secure together soft tissue of the body. The methods described above may also be used to mount orthopedic components onto bone, including cut guides, bone plates, and/or cerclage wires.

In some example embodiments, the pressurized gas source 38 and reservoir 52 are configured such that a single gas canister 38 has sufficient pressurized gas to drive several pins in multiple operations of the tool. The tool 10 may be configured to hold or fire more than one bone pin 20, in a "repeat fire" configuration. Example embodiments can include a handle that contains a pressurized gas source (for example, a 12 gram $C_{O2}$ cartridge) and a detachable barrel. The barrel can in some embodiments include a regulator to regulate the pressure delivered by, or held within, a reservoir chamber. In an example embodiment, a disposable cartridge can allow multiple pins to be inserted rapidly with simple manual indexing of the cartridge. The regulation of gas can allow many shots to be fired using a single 12 g cartridge.

A gas-powered bone fixation tool of the present disclosure can deliver, for example, metallic, polymeric, resorbable, or biological bone pins (also termed "darts") to simply and quickly reattach fracture fragments. The tool can be used in conjunction with conventional external fixation techniques at the remote location (such as a battlefield or medical emergency site) in preparation for transport to a more permanent medical facility. Due to the temporary nature of this fixation, final positioning of the fragments and Open Reduction with Internal Fixation (ORIF) techniques can be accomplished without requiring the removal of the initial fixation supplied by the bone fixation tool.

Pin or dart 20 is configured to be driven into bone fragments to secure the bone fragments together. Pin 20 may be constructed of a biocompatible polymer, and in certain embodiments, the biocompatible polymer may be biodegradable. For example, pin 20 may be constructed of a biodegradable polymer, such as polylactide (PLA). Pin 20 may also be constructed of polystyrene, poly methyl methacrylate, polycarbonate, or a fiber-reinforced polymer, for example. It also is within the scope of the present disclosure that pin 20 may be constructed of a biocompatible, non-ferrous metal, such as magnesium. Each pin 20 may have a length as small as approximately 0.5 inch, 0.6 inch, 0.7 inch, 0.8 inch, 0.9 inch, or less, and as large as approximately 1.0 inch, 1.1 inches, 1.2 inches, 1.3 inches, 1.4 inches, 1.5 inches, or more. Each pin 176 may have a diameter as small as approximately 0.03 inch, 0.04 inch, 0.05 inch, or 0.06 inch, and as large as approximately 0.07 inch, 0.08 inch, 0.09 inch, 0.10 inch, or more.

The use of polymer darts or pins 20 can offer adequate temporary fixation through use of a material that is easily revised and surgically manipulated. The properties of polymers allow definitive long-term fixation implants to be placed independent of the dart's location. Polymer darts can be easily drilled or cut and undesirable reductions can be disjoined for correction. Darts or pins 20 made from resorbable or biologic materials with biologic factors can be used to reduce infection and enhance healing.

The darts included in this disclosure can include a wide variety of designs and materials. Resorbable and non-resorbable polymeric materials are possible as well as shape-memory, liquid/curable or swelling/expandable materials. Trabecular Metal (TM) which has a porous or cellular nature promoting tissue adhesion can also be used in suitable darts. Dart design can include simple cylinders, barbs, rifling, heads, or screw-like threads. In some embodiments, darts ranging from 1-3 mm in diameter and roughly 2.5 cm long can be used.

Screw-type qualities can also be incorporated into the dart/tool design. Darts with a long helix can provide extra purchase in bone. A rifled barrel can also provide rotation of the dart during delivery. This rotation combined with a slightly helical dart design can increase dart penetration and reduce skiving (dart surface removal on entry).

In addition to darts, staples, sutures, and rosettes are other possible options available for use with a bone fixation tool of the type described herein. These projectiles are sometimes not suitable for use in other tools due to the nature of their design.

In an example embodiment, the configuration and manner of operation of the bone fixation tool allows the user to vary the length of the dart that is delivered. A significant amount of dart material can be provided in a tool and a variable stop or bumper can be used to control the travel of the dart and the piston or the needle formation. Once the tool has been fired, the excess dart material can easily be removed. A further example embodiment uses hydraulic dart delivery and enables a flexible barrel (or component thereof) to provide access to tight spaces, or be bent around a corner or bone formation, for example.

Bone pins or darts 20 can be provided in a suitable length to extend into a first bone fragment and end substantially flush with a second bone fragment to be joined together, for example. It is also within the scope of the present disclosure that pins 20 may have excess length that may be trimmed before or after pin 20 is implanted so that pin 20 ends substantially flush with the second bone fragment. For example, before pulling tool 10 away from bone fragments, pin 20 may be trimmed along the bone-facing end of the barrel to remove any excess length from pin 20. As another example, after pulling tool 10 away from bone fragments, pin 20 may be trimmed along a bone fragment to remove any excess length from pin 20.

In an example embodiment, a bone fixation tool may comprise two basic pieces: a handle and a barrel. The handle can serve simply as a means to accommodate a triggering device and be reusable during surgery but disposable after each procedure, for example. The barrel can contain all the necessary components to drive a dart, including but not limited to on-board power, a puncture device, safety components, a piston, a needle, a movable mass, and the dart itself. A wide variety of power sources is possible. Current options include compressed gasses ($CO_2$, nitrogen, air) but any containable and controllable power source can be utilized. Another method of providing impact force in other example embodiments can include the use of hydraulics. A contained fluid can be impacted, by a movable mass, or piston, causing amplified movement of the dart, for example.

When a dart insertion is needed or anticipated during surgery, an embodiment of the tool can used as follows. A barrel 26 (or portions thereof) can be installed (for example, by a snapping action) on or in to a handle, such as handle 40 for example. The act of connecting the barrel and handle can, in an example embodiment, cock the bone fixation tool, or pressurize an internal chamber (such as a reservoir 52 of the type described herein) and ready the tool for use. Once any safety lock on the tool is deactivated and the trigger is pulled, the dart is delivered. After the tool has been fired, the barrel can be removed and discarded. Another barrel can then be snapped into place and the procedure repeated. Upon completion of the surgery, all used barrels and the handle itself can be discarded, removing the need for subsequent cleaning, sterilization, autoclaving, or reusing of components.

In other example embodiments, the barrel can act as a "placement tool" and the handle can serve as a "drive means". The placement tool can separately be introduced into the surgical field and placed into position. During this procedure, the tool can be used to spread tissue or move items within the field. When proper tool placement is achieved, the drive means can be connected to the back of the tool and used to deploy the dart.

Advantages of the described bone fixation tool can include: simplicity of design; complete or partial disposability; minimal or no gas valving componentry; elimination of the need for a gas regulator; the ability to use of darts of various sizes with minimal waste of dart material; an ability to conveniently tailor power or pneumatic force based on individual dart sizes and designs; and, a decreased risk of user error through indexing, improper power settings, or gas handling. In addition, oblong or irregularly shaped complex projectiles can be used, such as staples, rosettes, or suture anchors.

Further advantages of the present disclosure can include improving inter-operative efficiencies associated with comminuted articular fractures. For example, technical goals can include: accurate reduction of fractures; effective stabilization for patient transport; unimpeded management of soft tissue injuries; quick and reliable injury treatment under harsh conditions; compatibility with staff skill levels; and reduced compromise of longer-term surgical options. In various embodiments, the bone fixation tool of the current disclosure can provide beneficial solutions to combat surgeons through the tool's ability to use a cost-effective, reliable, accessible, and quick change internal power supply; a lightweight, low profile, and easily transported design and package; an ability to be deployed quickly for rapid treatment delivery and be reloaded for continued use in the field. The temporary fixation of bone or soft tissue structures can significantly reduce the need for precise pre-op planning and can incorporate biologic or infection-controlling agents. The described means and methods of temporary fixation can minimize (and in some cases avoid entirely) the need to drill pilot holes, yet provide almost instantaneous fixation, and do not hinder the field of view during surgery. Polymeric pins can conveniently be screwed through during plate installation.

Embodiments of the present subject matter also include gas pressure regulators for bone fixation tools. With reference to accompanying FIGS. 7A-9B, example embodiments of a gas pressure regulator 100 are sized and configured to fit into a pressurized gas passageway in a bone fixation tool. The bone fixation tool may be of the type 10 described herein. As has been described, such tools may comprise a barrel or housing in which a piston can reciprocate axially to drive a bone pin (or other device) into a bone. Appropriate placement of such bone pins at a bone fracture site can secure bone fragments together to stabilize the fracture. In some embodiments, the piston has a head against which a pneumatic force generated by a gas pressure source can act. The example gas pressure regulators 100 are configured to regulate gas pressure within a bone fixation tool, as is described and illustrated more fully below.

Figure 7A:
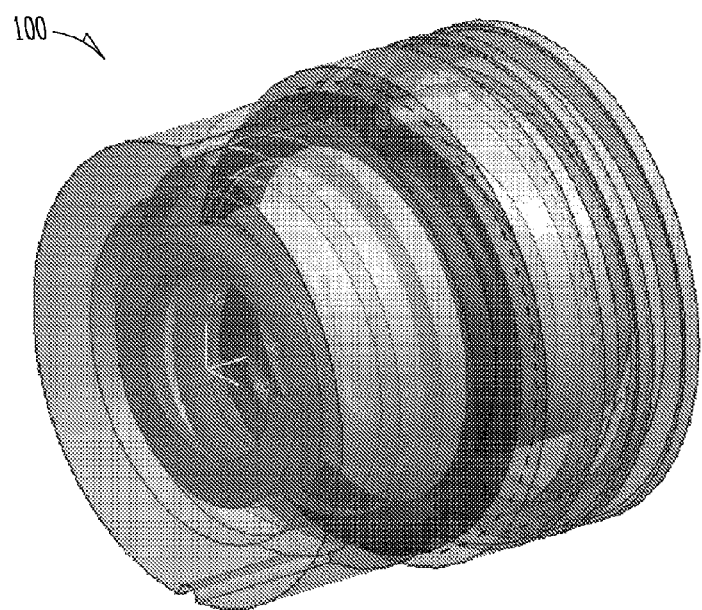
FIG. 7A shows a pictorial view of an assembled gas pressure regulator, according to example embodiments.
Figure 7B:
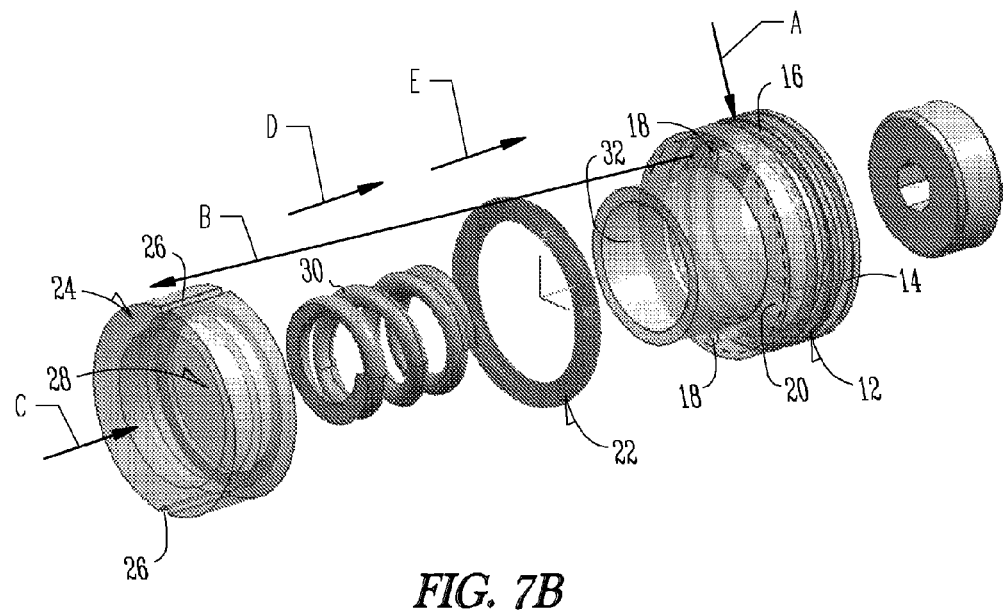
FIG. 7B shows an exploded pictorial view of the gas pressure regulator shown in FIG. 7A.

With reference to FIGS. 7A-7B, a gas pressure regulator 100 comprises a cylindrical regulator body 12. The body 12 includes one or more annular grooves around its periphery. In this case, two grooves 14 and 16 are provided. The first groove 14 can carry an O-ring seal (not shown) to seal the gas regulator 100 within a gas passageway in a bone fixation tool. The second annular groove 16 acts as an inlet passageway for the regulator and is in fluid communication with a tool gas pressure source (not shown). In an example embodiment, the second annular groove 16 is placed in fluid communication with the pressure source through appropriate porting in the tool.

At least one small diameter hole 18 is formed in the regulator body 12. In the illustrated example, two holes 18 place the second annular groove 16 in fluid communication with a front planar face 20 of the regulator body 12

The gas regulator 100 also comprises a second regulator seal in the form of an O-ring seal 22. The O-ring seal 22 can seal off the holes 18 in the planar face 20 of the regulator body 12. The O-ring seal 22 can be pushed against the planar face 20 to seal the holes 18 by the regulator mass 24, as is described more fully below. The gas regulator 100 also comprises a regulator mass 24 which carries ports 26 which are aligned with the small holes 18 when the gas regulator 100 is assembled in place within a bone fixation tool. The regulator mass 24 has a front face 28 against which pressurized gas escaping from the ports 26 can act to push the regulator mass 24 against the O-ring seal 22 to close off the small holes 18. A regulator spring 30 is interposed between the regulator mass 24 and the regulator body 12. In instances of high gas pressure or flow within the gas regulator 100, the O-ring seal 22 is squeezed between the regulator body 12 and mass 24 to seal the small holes 18 in the planar face 20 of the regulator body 12. In instances of low gas pressure or flow within the gas regulator 100, the force of the spring 30 acting outwardly along its axis displaces or unseals the O-ring seal 22 from the small holes 18 in the face 20, as is described more fully below. The spring 30 lies at one end against a rear face (not visible) of the regulator mass 24 and is disposed, at the other end, within an annular spring retainer 32 formed on the front side of the regulator body 12.

The example gas regulator 100 illustrated in FIGS. 7A-7B operates as follows in use. Pressurized gas enters the second annular groove 16 of the regulator body 12, as indicated generally by the arrow marked A. The gas flows through the small holes 18 of the regulator body 12 and around the O-ring seal 22. For purposes of this description, the O-ring seal 22 is initially displaced or unsealed from the planar face 20 of the regulator body 12 under action of the regulator spring 30 pushing the regulator mass 24 away from the regulator body 12. The gas passes through the small holes 18 and into the aligned ports 26. This movement is indicated generally by the arrow marked B. The gas then flows around the regulator mass 24 and the pressure generates a pneumatic force which acts on the face 28 of the regulator mass 24. This force is indicated generally by the vector arrow marked C. This inwardly directed force acts against and overcomes the outwardly directed force of the regulator spring 30 and causes a displacement of the regulator mass 24 towards the regulator body 12, shown by the arrow marked D. The displacement of the regulator mass 24 towards the regulator body 12 causes the O-ring seal 22 to be squeezed against the planar face 20, shown by the arrow marked E, to seal off the small holes 18 in the regulator body 12 and prevent the passage of further gas into and through the gas regulator 100. A metered volume of pressurized gas is expelled from the gas regulator 100 for use in the bone fixation tool to which it is fitted. The admission and expulsion of pressurized gas is regulated by the alternating inward and outward movement of the regulator mass 24 relative to the regulator body 12, and the resultant alternating opening and sealing of the small holes 18. If the pressure is too high, the small holes 18 are closed. If the pressure is too low, the small holes 18 are opened to place the holes 18 in fluid communication with the upstream gas pressure source and re-pressurize the gas regulator 100.

Figure 8A:
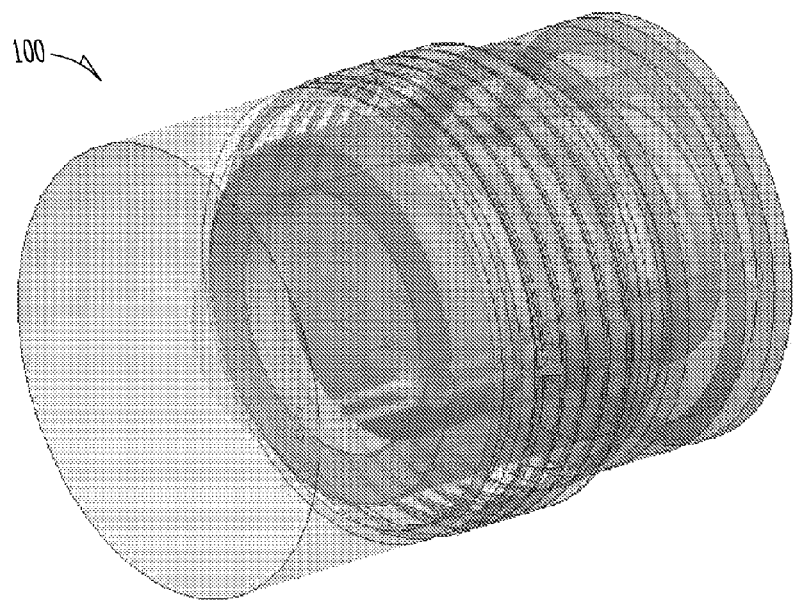
FIG. 8A shows a pictorial view of an assembled gas pressure regulator, according to example embodiments.
Figure 8B:
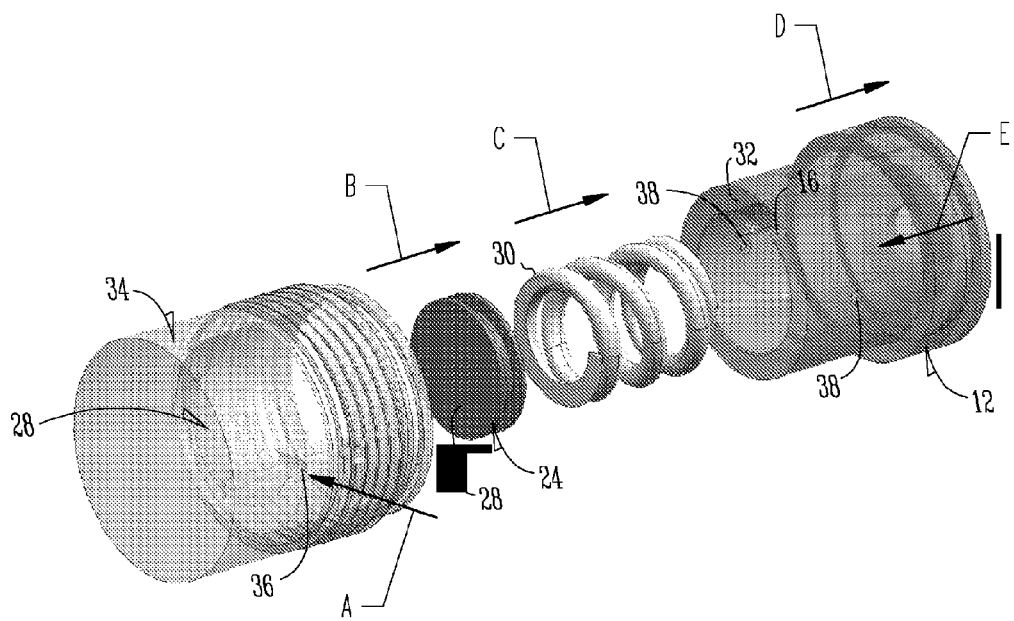
FIG. 8B shows an exploded pictorial view of the gas pressure regulator shown in FIG. 8A.

Reference is now made to FIGS. 8A-8B of the accompanying figures. In this example embodiment, the gas regulator 100 again comprises a regulator body 12, a regulator spring 30, and a regulator mass 24. The regulator body 12 includes an annular spring retainer 32, and the regulator mass 24 includes a front face 28 against which pressurized gas can act in the manner described below. The gas regulator 100 also comprises a regulator housing 34. The mass 24 and spring 30 can fit and move axially within the housing 34 and spring retainer 32, and the spring retainer 32 can fit within the housing 34 as shown.

The housing 34 has at least one inlet passageway in the form of small diameter hole 36 formed in a wall of the housing 34. The hole 36 is in fluid communication with a pressurized gas source (not shown) disposed upstream of the gas regulator 100. The fluid communication can be provided by appropriate porting provided in a gas passageway of a bone fixation tool in which the gas regulator 100 is fitted. The regulator body 12 has two further small holes 38 formed opposite one another in a wall of the body 12 and these allow exit of pressurized gas from the gas regulator 100 to a downstream side of the gas regulator 100.

The gas regulator 100 illustrated in FIGS. 8A-8B operates as follows. Pressurized gas enters the regulator housing 34 via the small diameter hole 36 and the gas passes into the interior volume of the housing 34. This gas entry is indicated by the arrow marked A in FIG. 8B. Pressure from the compressed gas acts on the front face 28 of the regulator mass 24 and this generates a pneumatic force vector indicated by the arrow marked B. The force generated by the compressed gas causes a prescribed displacement of the regulator mass 24 against the regulator spring 30. The direction of this displacement is indicated by the arrow marked C in FIG. 8B. Spring 30 is thus compressed and a restoring force is generated by the spring 30 which is temporarily overcome by the pneumatic force vector B. Continued displacement of the regulator mass 24 (in the direction of the arrow marked D) exposes the small holes 38 provided in the regulator body 12. The exposed holes 38 allow pressurized gas to vent from the gas regulator 100 and reduce the pressure inside it. Once sufficient gas has been vented, the restorative force of the compressed spring 30 can push the regulator mass 24 back in the other direction (indicated by the arrow marked E) to close the small holes 38 and allow pressure to build up in the gas regulator 100 once again by the admission of more gas through the upstream small hole 36 formed in the housing 34. Alternating cycles of opening and closing the small holes 38 regulates the gas pressure within the gas regulator 100 and the passage of compressed gas through it.

Figure 9A:
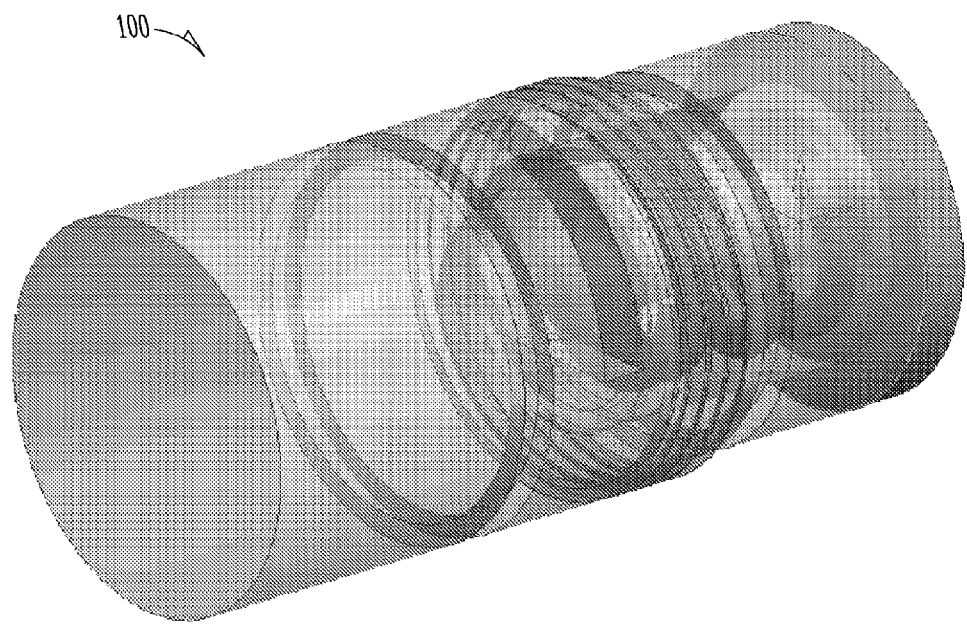
FIG. 9A shows a pictorial view of an assembled gas pressure regulator, according to example embodiments.
Figure 9B:
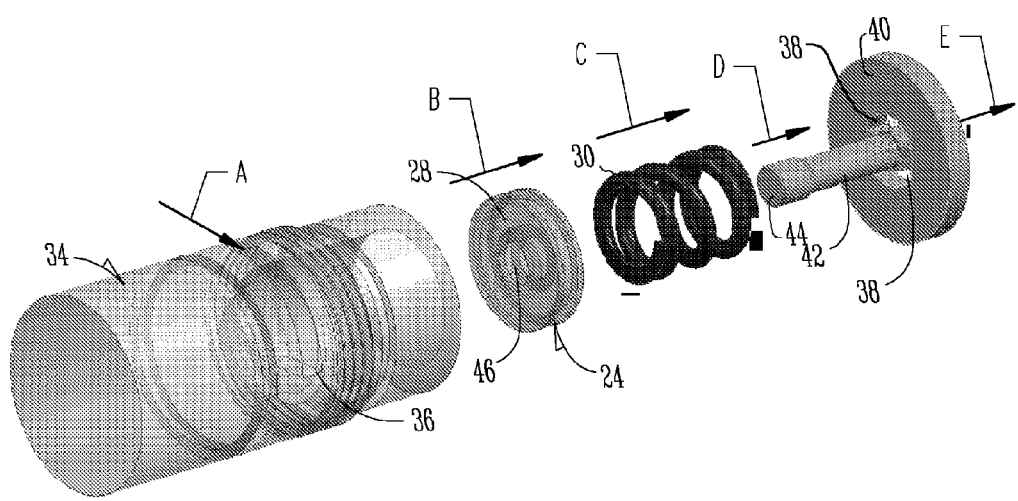
FIG. 9B shows an exploded pictorial view of the gas pressure regulator shown in FIG. 9A.

Reference is now made to FIGS. 9A-9B of the accompanying drawings. The illustrated gas regulator 100 includes a regulator housing 34, a regulator mass 24, a regulator spring 30, and a disc-shaped regulator base 40. The housing 34 includes an inlet passageway such as a small hole or, in this case, a slot 36 which allows pressurized gas to enter the interior volume of the housing 34 from an upstream pressurized gas source (not shown). The slot 36 can be placed in fluid communication with the upstream gas source by appropriate porting provided in a gas passageway of a bone fixation tool in which the regulator 100 is fitted.

The regulator base 40 is connected to a regulator stem 42 which includes a stem head 44 of greater cross-sectional diameter than the stem 42. The base 40 of the regulator 100 has holes, in this case curved apertures, 38 formed in it and these are disposed around the base of the stem 42. The curved apertures 38 allow pressurized gas to exit the regulator 100, as is described further below.

The regulator mass 24 has a front face 28 in which a central aperture 46 is provided. The walls of the central aperture 46 form a sliding sealed fit over the stem head 44 at least until the walls of the central aperture 46 pass clear of the stem head 44 as the mass 24 passes further down the smaller-diameter stem 42 against the action of the spring 30. Gas escaping through the gap formed between the stem head 44 and the central aperture 46 (once the aperture 46 is clear of the head 44) can pass downstream over the smaller diameter stem 42 and exit the regulator 100 through the curved apertures 38. The regulator spring 30 is interposed between the regulator mass 24 and the regulator base 40 as shown and, in similar fashion to the embodiments described above, therefore biases these two elements apart.

The gas regulator 100 illustrated in FIGS. 9A-9B operates as follows. Pressurized gas enters the regulator housing 34 through the slot 36 and passes into the interior volume of the housing 34. Gas entry into the housing 34 is indicated generally by the arrow marked A in FIG. 9B. Pressure from the gas exerts a pneumatic force against the face 28. This force is indicated by the force vector marked B in the same view. The force causes a prescribed displacement of the regulator mass 24 against the action of the regulator spring 30. The direction of this displacement is shown generally by the arrow marked C. The displacement of the regulator mass 24 is guided by the stem head 44 until the seal between the mass 24 and stem head 44 is broken as the mass 24 (and hence central aperture 46) passes clear of the head 44 and over the smaller-diameter stem 42. This action is indicated by the arrow marked D. Venting of gas though the broken seal reduces the pressure of the incoming gas and less force acts on the face 28. This allows the regulator spring 30 to push the mass 24 back in the opposite direction and reseal the mass 24 to the stem head 44. The vented gas exits the regulator 100 through the apertures 38 in the direction of the arrow marked E. Resealing of the mass 24 to the stem head 44 builds pressure within the regulator 100 again, and the cycle is repeated to regulate the gas pressure within the regulator 100 and the passage of compressed gas through it.

Reference is now made to FIGS. 10-25 of the accompanying drawings. The following associated description relates to bone darts and related aspects and gun configurations, according to example embodiments.

Bone Dart Materials

Bone dart materials can include metallic, porous, ceramic, and polymer materials, or can include a combination of such materials. Guide pins, which can serve to guide bone darts into a drilled hole for example, can include metallic material.

Porous materials can include Trabecular Metal™ ("TM"). Such materials can include materials called highly biocompatible materials. Highly biocompatible materials can include porous metallic structures such as porous tantalum, porous titanium, porous cobalt chrome, or porous zirconia dioxide, as well as polymeric scaffolds, or porous sections of aforementioned materials incorporating bone morphogenic proteins, platelet rich plasma, allografts, xenografts, autografts, or probiotic bacteria. Further details of TM can be found at tmt.zimmer.com, and http://www.zimmer.com/en-US/hcp/knee/our-science/trabecular-metal-technology.jspx.

Polymer materials can include PEEK (polyether ether ketone) materials, as well as body absorbable materials such as PLLA (polylactic acid), and so forth.

Combination materials can include bone darts having a hard metal tip, and a TM interior for example.

Bone Dart Geometry

Straight Bone Darts

Figure 10:
FIGS. 10-25 show schematic views of bone darts and related aspects and gun configurations, according to example embodiments.

With reference to FIG. 10, a bone dart can assume a straight cylindrical configuration, for example. This bone dart configuration can be useful for testing purposes, for example, to set a comparative "normal" or "base" anchoring strength of a bone dart gun, or bone dart is required.

Barbed or Ribbed Bone Darts

Figure 11A:
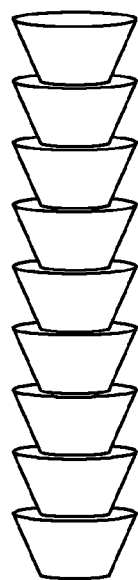
Figure 11B:
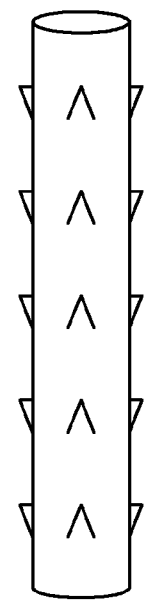

With reference to FIGS. 11A-11B, a barbed or ribbed bone dart can improve fixation of the dart in bone material. A headed dart can induce compression for improved fixation of the dart in bone material. Akin to a roofing nail, the flared head of such a dart can provide "bite" at the near side of a dart insertion site.

Expandable Bone Darts

Expandable bone darts can include shape-memory alloys or polymers. Expansion of the bone dart material after insertion can provided internal compression and increased fixation. Expansion can be activated by heat, fluid environment, or body temperature.

RF ID Tags

Bone darts can include RF ID tags for insertion into the body or bone materials.

Balls (Radiographic Markers)

Small balls can be inserted into the body or bone material. The process of insertion can be facilitated by a $CO_2$-powered (gas-powered) bone dart gun.

Hooked or Curved Bone Darts

Figure 12A:
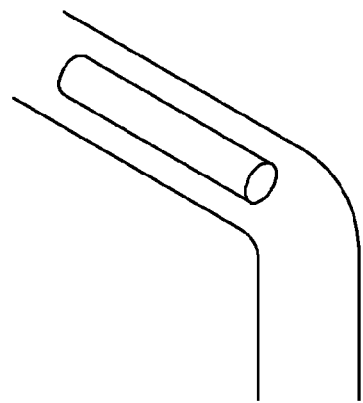
Figure 12B:
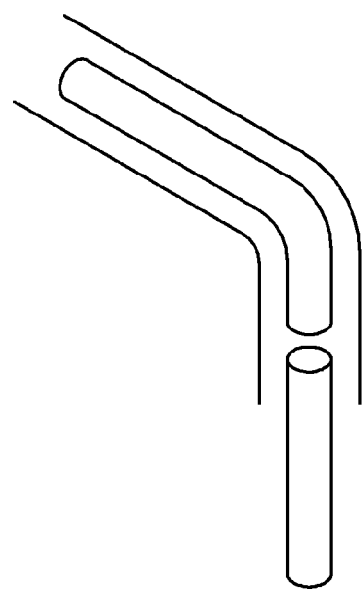

With reference to FIGS. 12A-12B, a curved delivery of a bone dart facilitates the ability to "shoot around corners". This can be very beneficial in tight spaces or where access is limited. A flexible bone dart or a flexible delivery needle or nozzle can be used to provide a curved delivery of a bone dart. Hydraulic apparatus can also be used in similar way.

Helix/Rifled Bone Dart

Figure 13:
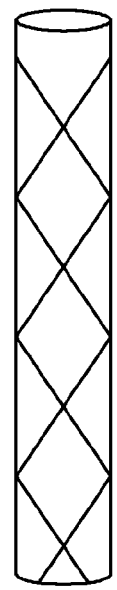

With reference to FIG. 13, a long helix or screw thread on the bone dart can induce rotation of the bone dart on insertion of the bone dart into bone.

Textured Dart Surface

Figure 14:

With reference to FIG. 14, a textured bone dart can include a shot-peened or grit-blasted bone dart. The increased surface roughness provides increased purchase of the bone dart in bone material and can more strongly resist pull-out.

In-Line Bone Darts

Bone darts can be provided in-line with each other for rapid firing out of a bone dart gun. Cut-to-length methods can be employed.

Lagged Bone Darts

Figure 15:
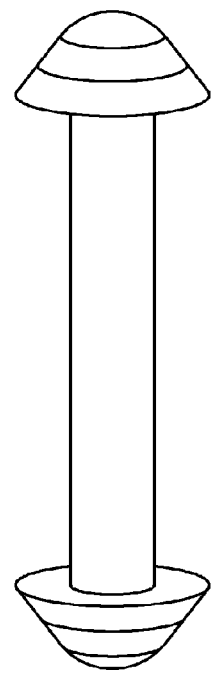

With reference to FIG. 15, a lagged bone dart can include a modified distal portion to induce compression across bone fractures. In addition to providing bite at a bone surface like the headed darts described above, "lag" style darts, when inserted into a bone, can resist movement in either direction.

Darts with Threaded Protrusion

Figure 16:
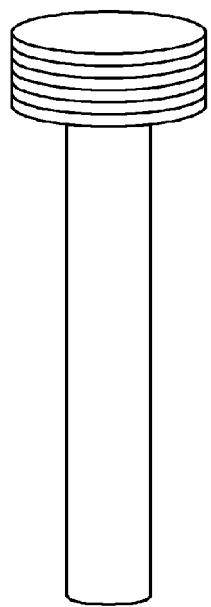

With reference to FIG. 16, a threaded distal or proximal end of a bone dart is left proud after insertion. This facilitates instant of future connection of surgical equipment or other material to the inserted bone dart. An alternate variation can include an eyelet instead of a threaded protrusion.

Tapered Bone Darts

Figure 17:

With reference to FIG. 17, if dart removal is desired, a tapered design can facilitate such removal. The insertion mechanics of a tapered dart are different to those of a straight cylindrical bone dart. For example, straight dart cylinders core out material whereas tapered darts employ hole-expansion mechanics.

Bone Dart Guns—Design Options

"Dual Chamber" Gun

A dual-chamber bone dart gun can include two pressurized gas cartridges (for example, $CO_2$ cartridges), each firing separately in operation of the gun. Loading a barrel to a gun can include puncturing the first gas cartridge. Firing the first gas cartridge can include puncturing the second gas cartridge.

"Double-Tap" Gun

Figure 18:
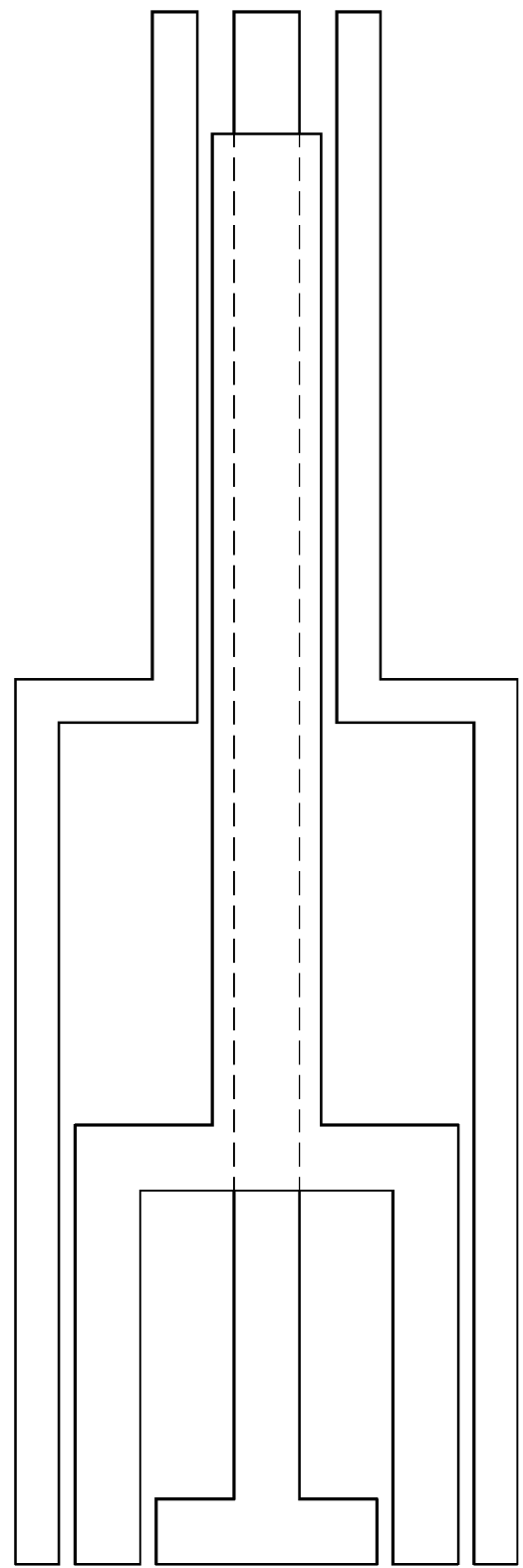

With reference to FIG. 18, a double-tap gun can include a two-part piston comprising two discrete parts or masses axially movable within a housing, as shown schematically in FIG. 18. Driving movement of the first inner mass out of the gun can create a pilot hole in a bone before insertion of a deliverable and/or a fluid by the second piston or mass. In an example embodiment, the face of the inner piston is relatively large and the piston is relatively light, the arrangement being such that that the inner piston can travel faster than the larger outer piston which has more mass. The opposite can also be achieved by balancing the surface areas and masses of the two pistons.

Integrated Tissue Graspers

A pair of graspers can be added to the front of a bone dart gun to allow for tissue manipulation. A secondary trigger on the gun can be used to actuate the graspers, separately from firing the gun. In an example embodiment, the graspers can allow a surgeon to manipulate tissue adjacent a bone fracture site, hold it in place, and insert a dart or other implant, into the bone.

Bone Dart Guns Using Exhaust Gasses

Suture Passing

Suture passers are commonly used in the sports medicine field and are manually actuated. Such manual tools require a significant trigger squeeze. A degree of automation would be of significant convenience.

The gas can be used to actuate a mechanism that can automatically pass a suture through tissue.

Knot Tying

Methods have been proposed to use gas to tie knots. An example embodiment of the present subject matter includes shooting pressurized gas into a series of tubes or fixtures and guiding a string or suture through the tube or fixture to form a knot. In an example embodiment, a knot is tied using a single-piece fixture.

Further Bone Dart Designs

Sutures

Leaving Sutures Protruding

Figure 19:
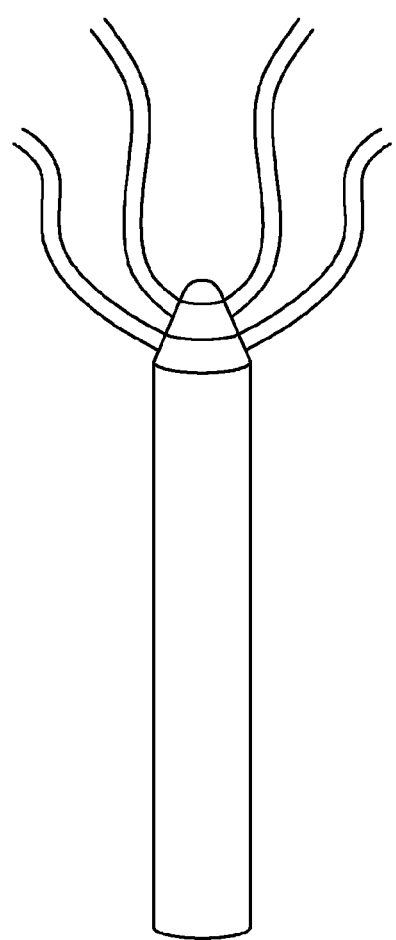

With reference to FIG. 19, a bone dart or anchor is preloaded with 1, 2 or 3 (any appropriate number) sutures fed through an eyelet. Anchor insertion may include the use of self-tapping threads or screws, expansion in a pre-drilled hole, or screwing into a pre-drilled hole. After insertion the protruding sutures are passed through tissue and tied accordingly.

Fire-in "Anchor" Portion

A bone dart of the type described just above may include an anchor portion that can be fired into, or rapidly inserted, into bone material. In this embodiment there is no need to pre-drill a hole into the bone material, or use self-tapping screws or threads.

Figure 20:
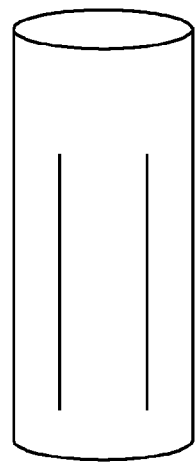

In an example embodiment shown schematically in FIG. 20, the cylinder in the view represents the housing or nozzle of a bone dart gun. Located within the nozzle is a "suture staple" which includes two darts that act like the legs of a staple. The legs can form an anchor portion for the bone dart. The darts (legs) are held together by a suture. When fired, the two legs are inserted into the bone and the suture is tightened or stretched, and can cinch down a desired object or tissue to the bone.

Figure 21:
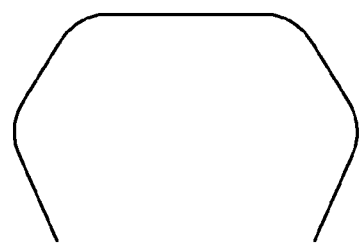
Figure 22:
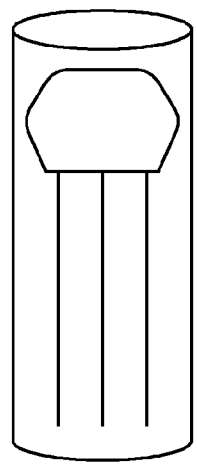
Figure 23:
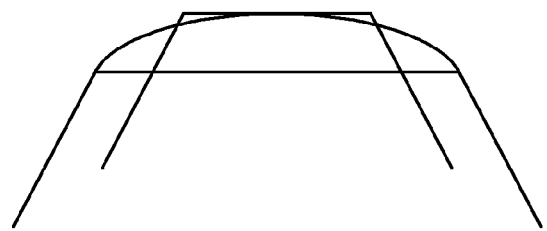
Figure 24:
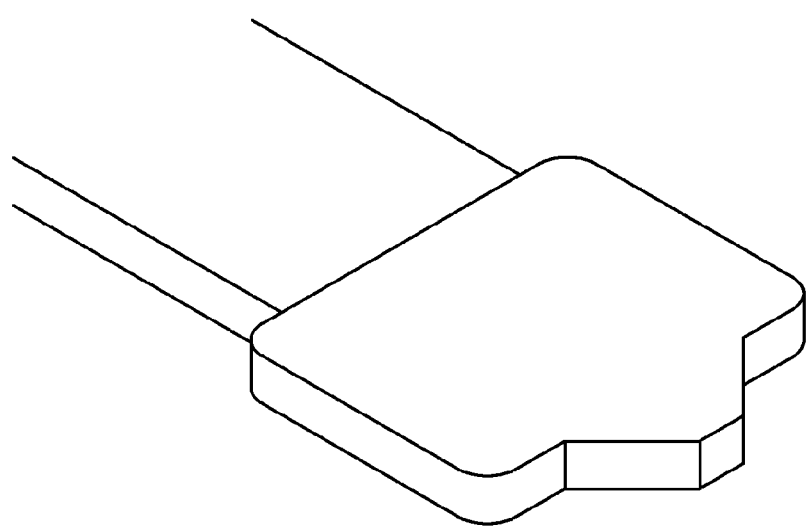

In an example embodiment depicted in FIG. 21, the legs are curved. This configuration can be achieved with shape memory materials of the type described further above, for example. The curved nature of the legs provides resistance to pull-out.

Mesh/Webbing

With reference to FIGS. 22-26, a meshed or webbed bone dart can include a staple configuration like embodiment discussed above. Instead of the suture connecting two legs together, a web or mesh can connect three or more legs together, for example, and compress or cinch an area between the multiple legs when inserted into a bone.

The mesh or web can open up or expand like a parachute (see FIG. 23) and can be pre-attached to the legs before the legs are inserted into bone. The deployed web or mesh (FIG. 24) can be used to secure a patch to tissue, for example.

Controlled Depth Stitching

Figure 25:
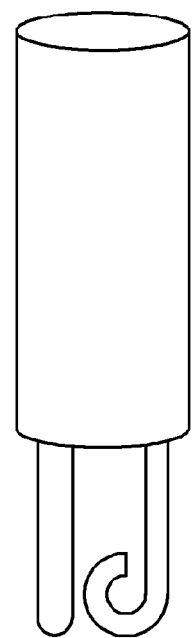

With reference to FIG. 25, alternating "push" and "pull" needles can be constituted by "bone darts" protruding from the end of a gun barrel as shown schematically in the view. The gun may be a stitching gun. The needles can move alternately to a controlled depth to pierce a woven (or non-woven) construct, for example, and push and pull fibers in the construct. The increased entanglement of fibers in the construct can improve the structural integrity or strength of the construct, and if the construct is a patch, improve the securement strength of bone fragments in a patched bone fracture, for example. This method can provide increased facility over methods including catching or pulling a single thread though a construct.

In an example embodiment, a stitching gun can be used in conjunction with a nonwoven material or patch in which the needles of the gun are used to push and pull fibers of the material or patch into adjacent objects or materials thus securing them together.

Dart with a Hollow Shell

In an example embodiment, a bone dart includes an internal structure which deforms or crushes and expands an outer shell to create purchase of the bone dart within a bone.

Injectable Materials and Bone Darts

Injectable bone dart materials can include epoxy materials, adhesive materials, curable polymer materials, and drug delivery materials.

Instead of using gas, for example, to drive a solid bone dart into a bone, an arrangement using a syringe can be employed to drive a plunger which in turn forces fluid out of a dart gun orifice. In example embodiments, the deliverables need not be solid and can include fluid materials.

A benefit of using gas power to drive a non-solid bone dart or injectable material is that viscous fluids and/or small delivery devices can be used with reduced concern for the level of manual force being applied by a user to depress a plunger.

Non-Limiting Embodiments

While the invention has been described with reference to specific embodiments, it will be understood by those skilled in the art that various changes may be made and equivalents may be substituted for the elements thereof without departing from the true spirit and scope of the invention. In addition, modifications may be made without departing from the essential teachings of the invention. Moreover, each of the non-limiting examples described herein can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A tool for stabilizing a fractured bone, comprising:
a barrel having a proximal end and a distal end, the distal end of the barrel including an opening;
a cartridge supported in the distal end of the barrel, the cartridge including a first elongate semi-cylindrical body having a first outer surface sized to fit within the distal end of the barrel and a first inner surface at least partly defining a passageway for receiving a bone pin configured to be driven into the fractured bone to stabilize the fractured bone, the passageway being sized to accommodate axial movement of the bone pin through the passageway while limiting radial movement of the bone pin in the passageway; and
a piston having a proximal end and a distal end and is configured to translate axially relative to the barrel, the proximal end of the piston including a head and the distal end of the piston including a needle formation provided on a support member, the support member having a second elongate semi-cylindrical body having a second outer surface and a second inner surface such that the second elongate semi-cylindrical body is complementary to the first elongate semi-cylindrical body of the cartridge to fit within the distal end of the barrel, wherein, when the first and second inner surfaces directly oppose each other, the first and second outer surfaces define a shape that corresponds to the distal end of the barrel, and wherein the needle formation is sized for receipt within the passageway of the cartridge, the needle formation configured to apply sufficient force to the bone pin to drive the bone pin axially from the barrel and into the fractured bone.

2. The tool of claim 1, wherein the cartridge includes a single passageway for receiving a single bone pin configured to be driven into the fractured bone to stabilize the fractured bone.

3. The tool of claim 1, further including a pressurized gas source for supplying a pneumatic force to the head of the piston to axially translate the piston relative to the barrel.

4. The tool of claim 3, further including a handle configured to receive at least the pressurized gas source.

5. The tool of claim 1, further including a handle configured to support at least the barrel.

6. The tool of claim 1, further including a handle, wherein the handle includes a housing or housing portion axially aligned with a longitudinal axis of the barrel, the housing or housing portion including a connection port to which a pressurized gas source can be coupled.

7. The tool of claim 1, further including a handle configured to be coupled to the barrel.

8. The tool of claim 1, wherein the piston is axially translatable within the barrel.

9. The tool of claim 1, further comprising a trigger assembly for releasing the piston.

10. The tool of claim 9, wherein the trigger assembly includes a component that extends through a side wall of the barrel.

11. The tool of claim 10, wherein the component is movable in and out of the side wall of the barrel to restrain and permit, respectively, axial translation of the piston.

12. The tool of claim 9, further including a pressurized gas source configured to supply pneumatic force to the head of the piston when the piston is restrained by the trigger assembly, and when driving the bone pin into the fractured bone.

13. The tool of claim 12, further including a reservoir for holding gas under pressure while the piston is restrained by the trigger assembly.

14. The tool of claim 13, further including a puncture device operable to puncture, release or transfer gas from the pressurized gas source into the reservoir.

15. The tool of claim 1, wherein the barrel includes one or more exhaust ports in a side wall thereof.

16. A system for stabilizing a fractured bone, comprising:
a tool according to claim 1;
at least one bone pin; and
a set of instructions for using one or both of the tool or at least one bone pin.

17. The system of claim 16, wherein the at least one bone pin is a polymeric bone pin, or includes polymeric material.

18. A tool for stabilizing a fractured bone, comprising:
a barrel having a proximal end and a distal end, the barrel including a piston housing located at the proximal end and a tubular portion extending from the piston housing and terminating at a distal end of the barrel;
a cartridge located at the distal end of the barrel within the tubular portion, the cartridge including a first elongate semi-cylindrical body having a first outer surface sized to fit within the distal end of the tubular portion and a first inner surface at least partly defining a passageway for receiving a bone pin configured to be driven into the fractured bone to stabilize the fractured bone, the passageway being sized to accommodate axial movement of the bone pin through the passageway while limiting radial movement of the bone pin in the passageway;

a piston having a proximal end and a distal end and is configured to translate axially relative to the barrel, the proximal end of the piston including a head and the distal end of the piston including a needle formation provided on a support member, the support member having a second elongate semi-cylindrical body having a second outer surface and a second inner surface such that the second elongate semi-cylindrical body is complementary to the first elongate semi-cylindrical body of the cartridge to fit within the distal end of the barrel, wherein, when the first and second inner surfaces directly oppose each other, the first and second outer surfaces define a shape that corresponds to the distal end of the barrel, and wherein the needle formation is sized for receipt within the passageway of the cartridge, the needle formation configured to apply sufficient force to the bone pin to drive the bone pin axially from the barrel and into the fractured bone;

a pressurized gas source for supplying a pneumatic force to the head of the piston to axially translate the piston relative to the barrel; and a trigger assembly for releasing the piston.

19. The tool of claim 18, wherein the cartridge defines a single passageway for receiving a single bone pin configured to be driven into the fractured bone to stabilize the fractured bone.

\* \* \* \* \*